US005821051A

United States Patent [19]
Androphy et al.

[11] Patent Number: 5,821,051
[45] Date of Patent: Oct. 13, 1998

[54] E6 BINDING PROTEINS

[75] Inventors: Elliot Androphy, Natick; Jason J. Chen, Boston, both of Mass.

[73] Assignee: New England Medical Center Hospitals, Boston, Mass.

[21] Appl. No.: 840,683

[22] Filed: Apr. 29, 1997

Related U.S. Application Data

[63] Continuation of Ser. No. 273,059, Jul. 8, 1994, abandoned.

[51] Int. Cl.⁶ .................................................. C12Q 1/70
[52] U.S. Cl. .............................. 435/5; 530/350; 530/352; 530/357; 530/358
[58] Field of Search ................................ 435/5; 530/350, 530/352, 357, 358

[56] References Cited

U.S. PATENT DOCUMENTS

| | | | |
|---|---|---|---|
| 5,464,936 | 11/1995 | Butchan et al. | 530/350 |
| 5,532,348 | 7/1996 | Huibregtse et al. | 536/23.5 |

OTHER PUBLICATIONS

Keen et al Oncogene 9:1493 1994 (May).
Hartman et al., "The complete primary structure of rat chaperonin 10 reveals a putative βαβ nucleotide–binding domain with homology to p21ras", *Biochimica et Biophysica Acta* 1164:219–222 (1993).
Ryan et al., "Isolation of a cDNA clone specifying rat chaperonin 10, a stress–inducible mitochondrial matrix protein synthesised without a cleavable presequence", FEBS Letters, 337:152–156 (Jan. 1994).
Arbeit, J.M. et al., "Neuroepithelial Carcinomas in Mice Transgenic with Human Papillomavirus Type 16 E6/E7 ORFs" *Am. J. Pathol.*, vol. 142, No. 4, pp. 1187–1197, 1993.
Chien, C.–T. et al., "The two–hybrid system: A method to identify and clone genes for proteins that interact with a protein of interest" *Proc. Natl. Acad. Sci.*, vol. 88, pp. 9578–9582, Nov. 1991.
Cole, S.T. and O. Danos, "Nucleotide Sequence and Comparative Analysis of the Human Papillomavirus Type 18 Genome" *J. Mol. Biol.*, vol. 193, pp. 599–608, 1987.
Crook, T. et al., "Degradation of p53 Can Be Targeted by HPV E6 Sequences Distinct from Those Required for p53 Binding and Trans–Activation" *Cell*, vol. 67, pp. 547–556, 1991.
Fields, S. and O. Song, "A novel genetic system to detect protein–protein interactions" *Nature*, vol. 336, pp. 495–496, 1988.
Kaebling, M. et al., "Loss of heterozygosity on chromosome 17p and mutant p53 in HPV–negative cervical carcinomas" *The Lancet*, vol. 340, pp. 140–142, 18 Jul. 1992.
Gu, Z. et al., "DNA damage induced p53 mediated transcription is inhibited by human papillomavirus typ 18 E6" *Oncogene*, vol. 9, pp. 629–633, 1994.
Hoppe–Seyler, F. and K. Butz, "Cellular Control of Human Papillomavirus Oncogene Transcription" *Molecular Carcinogenesis*, vol. 10, pp. 134–141, 1994.

Howley, P.M., "Role of the Human Papillomaviruses in Human Cancer" *Cancer Research* (Suppl.), vol. 51, pp. 5019s–5022s, 15 Sep. 1991.
Huibregtse, J.M. et al., "A cellular protein mediates association of p53 with the E6 oncoprotein of human papillomavirus types 16 or 18" *The EMBO Journal*, vol. 10, No. 13, pp. 4129–4135, 1991.
Huibregtse, J.M. et al., "Cloning and Expression of the cDNA for E6–AP, a Protein That Mediates the Interaction of the Human Papillomavirus E6 Oncoprotein with p53" *Molecular and Cellular Biology*, vol. 13, No. 2, pp. 775–784, Feb. 1993.
Kim, K.H. et al., "Expression and Localization of Human Papillomavirus Type 16 E6 and E7 Open Reading Frame Proteins in Human Epidermal Keratinocyte" *Yonsei Medical Journal*, vol. 35, No. 1, pp. 1–9, 1994.
Lamberti, C. et al., "Transcriptional activation by the papillomavirus E6 zinc finger oncoprotein" *The EMBO Journal*, vol. 9, No. 6, pp. 1907–1913, 1990.
Lechner, M.S. et al., "Inhibition of p53 DNA Binding by Human Papillomavirus E6 Proteins" *Journal of Virology*, vol. 68, No. 7, pp. 4262–4273, Jul. 1994.
Liang, X.H. et al., "Co–localization of the tumor–suppressor protein p53 and human papillomavirus E6 protein in human cervical carcinoma cell lines" *Oncogene*, vol. 8, pp. 2645–2652, 1993.
May, E. et al., "Endogenous HeLa p53 proteins are easily detected in HeLa cells transfected with mouse deletion mutant p53 gene" *Oncogene*, vol. 6, pp. 1363–1365, 1991.
Mietz, J.A. et al., "The transcriptional transactivation function of wild–type p53 is inhibited by SV40 large T–antigen and by HPV–16 E6 oncoprotein" *The EMBO Journal*, vol. 11, No. 13, pp. 5013–5020, 1992.
Morrissey, L.C. et al., "trans Activation by the Bovine Papillomavirus E2 Protein in *Saccharomyces cerevisiae*" *Journal of Virology*, vol. 63, No. 10, pp. 4422–4425, Oct. 1989.
Scheffner, M. et al., "The E6 Oncoprotein Encoded by Human Papillomavirus Types 16 and 18 Promotes the Degradation of p53" *Cell*, vol. 63, pp. 1129–1136, 21 Dec. 1990.

(List continued on next page.)

*Primary Examiner*—Jeffrey Stucker
*Attorney, Agent, or Firm*—Louis Myers; Lahive & Cockfield

[57] ABSTRACT

An assay for screening test compounds to indentify agents which modulate the binding of an E6-BP polypeptide with a papilloma virus E6 protein. The assay includes combining, as a cell-free system, an E6-binding protein or fragment thereof which binds to the E6 protein, and a test compound, and detecting the formation of a complex which includes the E6 protein and the E6-binding protein. A change in the formation of the complex in the presence of the test compound is indicative of an agent that modulates interaction between an E6 and an E6-binding protein.

31 Claims, 1 Drawing Sheet

OTHER PUBLICATIONS

Scheffner, M. et al., "The HPV–16 E6 and E6–AP Complex Functions as a Ubiquitin–Protein Ligase in the Ubiquitination of p53" *Cell*, vol. 75, pp. 495–505, 5 Nov. 1993.

Scheffner, M. et al., "Interaction of the Human Papillomavirus Type 16 E6 Oncoprotein with Wild–Type and Mutant Human p53 Proteins" *Journal of Virology*, vol. 66, No. 8, pp. 5100–5105, Aug. 1992.

Sedman, S.A. et al., "Mutant p53 Can Substitute for Human Papillomavirus Type 16 E6 in Immortalization of Human Keratinocytes but Does Not Have E6–Associated trans–Activation or Transforming Activity" *Journal of Virology*, vol. 66, No. 7, pp. 4201–4208, Jul. 1992.

Storey, A. and L. Banks, "Human papillomavirus type 16 E6 gene cooperates with EJ–ras to immortalize primary mouse cells" *Oncogene*, vol. 8, pp. 919–924, 1993.

E6 BINDING PROTEINS

This application is a file wrapper continuation of application Ser. No. 08/273,059 filed on Jul. 8, 1994, now abandoned.

GOVERNMENT FUNDING

Work described herein was supported in part by funding from the National Institute of Health, Grant number CA 44174. The United States Government has certain rights in the invention.

BACKGROUND OF THE INVENTION

Papillomaviruses (PV) have been linked to widespread, serious human diseases, especially carcinomas of the genital and oral mucosa. It is estimated that there are currently somewhere in the neighborhood of tens of millions of women who suffer from human papilloma virus (HPV) infection of the genital tract. Many of these women eventually develop cancer of the cervix. For example, it has been estimated that about twenty percent (20%) of all cancer deaths in women worldwide are from cancers which are associated with HPV. It has also been estimated that 90% of all cervical cancer is linked to HPV.

Papillomaviruses induce benign, dysplastic and malignant hyperproliferations of skin or mucosal epithelium (see, for example, Mansur and Androphy, (1993) *Biochim Biophys Acta* 1155:323–345; Pfister (1984) *Rev. Physiol. Biochem. Pharmacol.* 99:111–181; and Broker et al. (1986) *Cancer Cells* 4:17–36, for reviews of the molecular, cellular, and clinical aspects of the papillomaviruses). Almost 70 human papillomavirus types have been identified, and different papillomavirus types are known to cause distinct diseases, Pfister, (1987) *Adv. Cancer Res.,* 48:113–147, Syrjanen, (1984) *Obstet. Gynecol. Survey* 39:252–265. Human papillomaviruses (HPVs) are a heterogeneous group of DNA tumor viruses associated with hyperplastic (warts, condylomata), pre-malignant and malignant lesions (carcinomas) of squamous epithelium. For example, HPV types 1 and 2 cause common warts, and types 6 and 11 cause warts of the external genitalia, anus and cervix. HPV, types 16, 18, 31 and 33 have been isolated from the majority of cervical cancers with HPV-16 present in about 50 percent of all cervical cancers. These HPV's are referred to as "high risk". While HPV 6 and 11 are the most common isolates for cervical warts, these infections rarely progress to invasive cancer, and therefore these HPB's are referred to as "low risk".

Studies of viral gene expression in carcinomas suggest the importance of two HPV encoded proteins, E6 and E7, in malignant development and these proteins have been shown to encode transforming and immortalizing activities. The two proteins show some functional resemblance to the transforming proteins of other small DNA tumor viruses such as adenovirus and SV40. E7 shares functional and structural features with the adenovirus E1A proteins. Like Ad E1A and the large T proteins of the polyomaviruses, E7 can complex pRB. Likewise, the E6 oncoprotein encoded by the "high risk" HPV's can form a complex with p53. In vitro, E6 promotes the degradation of p53 and this degradation involves the ubiquitin-dependent protease system. The selective degradation of cellular negative regulatory proteins such as p53 regulatory functions provides an explanation of the action for dominant acting oncoproteins. The relevance of the inactivation of the normal functions of pRB and p53 in human cervical carcinogenesis has recently been demonstrated by the analysis of these two genes and their products in a series of HPV-positive and HPV-negative cell lines. These studies support the notion that the inactivation of the normal functions of the tumor suppressor proteins pRB and p53 are important steps in human cervical carcinogenesis, either by mutation or through complex formation with HPV E6 and E7 oncoproteins.

SUMMARY OF THE INVENTION

The present invention relates to the discovery in eukaryotic cells, particularly human cells, of novel protein-protein interactions between the papillomavirus transforming protein E6 and certain cellular proteins, referred to hereinafter as "E6-binding proteins" or "E6-BP".

In general, the invention features a E6-BP$^{SD-7}$ polypeptide, preferably a substantially pure preparation of an E6-BP$^{SD-7}$ polypeptide, or a recombinant E6-BP$^{SD-7}$ polypeptide. In preferred embodiments: the polypeptide has biological activity, e.g., it specifically binds a papillomavirus E6 protein; the polypeptide has an amino acid sequence at least 60%, 80%, 90% or 95% homologous to the amino acid sequence in SEQ ID No: 8; the polypeptide has an amino acid sequence essentially the same as the amino acid sequence in SEQ ID No: 8; the polypeptide is at least 5, 10, 20, 50, 100, or 150 amino acids in length; the polypeptide comprises at least 5, preferably at least 10, more preferably at least 20, more preferably at least 50, 100, or 150 contiguous amino acids from SEQ ID No: 8; the E6-BP$^{SD-7}$ polypeptide is either, an agonist or an antagonist of a biological activity of an E6-PB, e.g., of the regulation of cell proliferation.

In preferred embodiments the invention includes E6-binding proteins with antagonistic activity, and which preferably are capable of: suppressing tumor growth, e.g. in a tumor cell in which endogenous E6-BP is misexpressed; suppressing growth of papillomavirus-infected cells, e.g. HPV-infected cells; blocking or inducing apoptosis; inhibiting growth of a papillomavirus-infected cell, e.g. an HPV-infected cell, e.g. a high-risk HPV infected cell, e.g. and HPV-16, -18, -31, or -33 infected cell, e.g. a bovine papillomavirus (BPV)-infected cell; inhibiting infection of a cell by a papillomavirus, e.g. an HPV, e.g. a high-risk HPV, e.g. and HPV-16, -18, -31, or -33, e.g. a bovine papillomavirus (BPV); inhibiting transformation of a cell by a papillomavirus, e.g. an HPV, e.g. a high-risk HPV, e.g. and HPV-16, -18, -31, or -33, e.g. a bovine papillomavirus; or inhibiting immortalization of a cell, e.g. a human cell, by a papillomavirus, e.g. an HPV, e.g. a high-risk HPV, e.g. and HPV-16, -18, -31, or -33, e.g. a bovine papillomavirus.

In a preferred embodiment, a peptide having at least one biological activity of the subject E6-BP$^{SD-7}$ polypepide may differ in amino acid sequence from the sequence in SEQ ID No: 8, but such differences result in a modified protein which functions in the same or similar manner as the native E6-binding protein or which has the same or similar characteristics of the native E6-binding protein.

In yet other preferred embodiments, E6-binding protein is a recombinant fusion protein which includes a second polypeptide portion, e.g., a second polypeptide having an amino acid sequence unrelated to a protein represented by one of SEQ ID Nos: 8–14, e.g. the second polypeptide portion is glutathione-S-transferase, e.g. the second polypeptide portion is a DNA binding domain, e.g. the second polypeptide portion is a polymerase activating domain, e.g. the fusion protein is functional in a two-hybrid assay.

In preferred embodiments of a protein homologous to SEQ ID No: 8, the protein has a molecular weight of approximately 50 kilodaltons, e.g. in the range of 45–55 kD, e.g. in the range of 48–52 kD.

In preferred embodiments: the peptide includes at least 1, 2, 3, or 5, and preferably 10, 20, and 30, amino acid residues from residues 1–133 of Sequence ID No: 8.

Yet another aspect of the present invention concerns an immunogen comprising an E6-BP polypeptide in an immunogenic preparation, the immunogen being capable of eliciting an immune response specific for said E6-BP polypeptide; e.g. a humoral response, e.g. an antibody response; e.g. a cellular response. In preferred embodiments, the immunogen comprising an antigenic determinant, e.g. a unique determinant, from a protein represented by SEQ ID No: 8.

A still further aspect of the present invention features an antibody preparation specifically reactive with an epitope of the E6-BP immunogen.

In another aspect, the invention features a E6-BP$^{SD-8}$ polypeptide, preferably a substantially pure preparation of an E6-BP$^{SD-8}$ polypeptide, or a recombinant E6-BP$^{SD-8}$ polypeptide. In preferred embodiments: the polypeptide has biological activity, e.g., it specifically binds a papillomavirus E6 protein; the polypeptide has an amino acid sequence at least 60%, 80%, 90% or 95% homologous to the amino acid sequence in SEQ ID No: 9; the polypeptide has an amino acid sequence essentially the same as the amino acid sequence in SEQ ID No: 9; the polypeptide is at least 5, 10, 20, 50, 100, or 150 amino acids in length; the polypeptide comprises at least 5, preferably at least 10, more preferably at least 20, more preferably at least 50, 100, or 150 contiguous amino acids from SEQ ID No: 9; the E6-BP$^{SD-8}$ polypeptide is either, an agonist or an antagonist of a biological activity of an E6-PB, e.g., of the regulation of cell proliferation.

In preferred embodiments the invention includes E6-binding proteins with antagonistic activity, and which preferably are capable of: suppressing tumor growth, e.g. in a tumor cell in which endogenous E6-BP is misexpressed; suppressing growth of papillomavirus-infected cells, e.g. HPV-infected cells; blocking or inducing apoptosis; inhibiting growth of a papillomavirus-infected cell, e.g. an HPV-infected cell, e.g. a high-risk HPV infected cell, e.g. and HPV-16, -18, -31, or -33 infected cell, e.g. a bovine papillomavirus (BPV)-infected cell; inhibiting infection of a cell by a papillomavirus, e.g. an HPV, e.g. a high-risk HPV, e.g. and HPV-16, -18, -31, or -33, e.g. a bovine papillomavirus (BPV); inhibiting transformation of a cell by a papillomavirus, e.g. an HPV, e.g. a high-risk HPV, e.g. and HPV-16, -18, -31, or -33, e.g. a bovine papillomavirus; or inhibiting immortalization of a cell, e.g. a human cell, by a papillomavirus, e.g. an HPV, e.g. a high-risk HPV, e.g. and HPV-16, -18, -31, or -33, e.g. a bovine papillomavirus.

In a preferred embodiment, a peptide having at least one biological activity of the subject E6-BP$^{SD-8}$ polypepide may differ in amino acid sequence from the sequence in SEQ ID No: 9, but such differences result in a modified protein which functions in the same or similar manner as the native E6-binding protein or which has the same or similar characterstics of the native E6-binding protein.

In yet other preferred embodiments, E6-binding protein is a recombinant fusion protein which includes a second polypeptide portion, e.g., a second polypeptide having an amino acid sequence unrelated to a protein represented by one of SEQ ID Nos: 8–14, e.g. the second polypeptide portion is glutathione-S-transferase, e.g. the second polypeptide portion is a DNA binding domain, e.g. the second polypeptide portion is a polymerase activating domain, e.g. the fusion protein is functional in a two-hybrid assay.

Yet another aspect of the present invention concerns an immunogen comprising an E6-BP polypeptide in an immunogenic preparation, the immunogen being capable of eliciting an immune response specific for said E6-BP polypeptide; e.g. a humoral response, e.g. an antibody response; e.g. a cellular response. In preferred embodiments, the immunogen comprising an antigenic determinant, e.g. a unique determinant, from a protein represented by SEQ ID No: 9.

A still further aspect of the present invention features an antibody preparation specifically reactive with an epitope of the E6-BP immunogen.

In another aspect, the invention features a E6-BP$^{SD-12}$ polypeptide, preferably a substantially pure preparation of an E6-BP$^{SD-12}$ polypeptide, or a recombinant E6-BP$^{SD-12}$ polypeptide. In preferred embodiments: the polypeptide has biological activity, e.g., it specifically binds a papillomavirus E6 protein; the polypeptide has an amino acid sequence at least 60%, 80%, 90% or 95% homologous to the amino acid sequence in SEQ ID No: 10; the polypeptide has an amino acid sequence essentially the same as the amino acid sequence in SEQ ID No: 10; the polypeptide is at least 5, 10, 20, 50, 100, or 150 amino acids in length; the polypeptide comprises at least 5, preferably at least 10, more preferably at least 20, more preferably at least 50, 100, or 150 contiguous amino acids from SEQ ID No: 10; the E6-BP$^{SD-12}$ polypeptide is either, an agonist or an antagonist of a biological activity of an E6-PB, e.g., of the regulation of cell proliferation.

In preferred embodiments the invention includes E6-binding proteins with antagonistic activity, and which preferably are capable of: suppressing tumor growth, e.g. in a tumor cell in which endogenous E6-BP is misexpressed; suppressing growth of papillomavirus-infected cells, e.g. HPV-infected cells; blocking or inducing apoptosis; inhibiting growth of a papillomavirus-infected cell, e.g. an HPV-infected cell, e.g. a high-risk HPV infected cell, e.g. and HPV-16, -18, -31, or -33 infected cell, e.g. a bovine papillomavirus (BPV)-infected cell; inhibiting infection of a cell by a papillomavirus, e.g. an HPV, e.g. a high-risk HPV, e.g. and HPV-16, -18, -31, or -33, e.g. a bovine papillomavirus (BPV); inhibiting transformation of a cell by a papillomavirus, e.g. an HPV, e.g. a high-risk HPV, e.g. and HPV-16, -18, -31, or -33, e.g. a bovine papillomavirus; or inhibiting immortalization of a cell, e.g. a human cell, by a papillomavirus, e.g. an HPV, e.g. a high-risk HPV, e.g. and HPV-16, -18, -31, or -33, e.g. a bovine papillomavirus.

In a preferred embodiment, a peptide having at least one biological activity of the subject E6-BP$^{SD-12}$ polypepide may differ in amino acid sequence from the sequence in SEQ ID No: 10, but such differences result in a modified protein which functions in the same or similar manner as the native E6-binding protein or which has the same or similar characterstics of the native E6-binding protein.

In yet other preferred embodiments, E6-binding protein is a recombinant fusion protein which includes a second polypeptide portion, e.g., a second polypeptide having an amino acid sequence unrelated to a protein represented by one of SEQ ID Nos: 8–14, e.g. the second polypeptide portion is glutathione-S-transferase, e.g. the second polypeptide portion is a DNA binding domain, e.g. the second polypeptide portion is a polymerase activating domain, e.g. the fusion protein is functional in a two-hybrid assay.

Yet another aspect of the present invention concerns an immunogen comprising an E6-BP polypeptide in an immunogenic preparation, the immunogen being capable of eliciting an immune response specific for said E6-BP polypeptide; e.g. a humoral response, e.g. an antibody response; e.g. a cellular response. In preferred embodiments, the immunogen comprising an antigenic determinant, e.g. a unique determinant, from a protein represented by SEQ ID No: 10.

A still further aspect of the present invention features an antibody preparation specifically reactive with an epitope of the E6-BP immunogen.

In another aspect, the invention features a E6-BP$^{SD-16}$ polypeptide, preferably a substantially pure preparation of an E6-BP$^{SD-16}$ polypeptide, or a recombinant E6-BP$^{SD-16}$ polypeptide. In preferred embodiments: the polypeptide has biological activity, e.g., it specifically binds a papillomavirus E6 protein; the polypeptide has an amino acid sequence at least 60%, 80%, 90% or 95% homologous to the amino acid sequence in SEQ ID No: 11; the polypeptide has an amino acid sequence essentially the same as the amino acid sequence in SEQ ID No: 11; the polypeptide is at least 5, 10, 20, 50, 100, or 150 amino acids in length; the polypeptide comprises at least 5, preferably at least 10, more preferably at least 20, more preferably at least 50, 100, or 150 contiguous amino acids from SEQ ID No: 11; the E6-BP$^{SD-16}$ polypeptide is either, an agonist or an antagonist of a biological activity of an E6-PB, e.g., of the regulation of cell proliferation.

In preferred embodiments the invention includes E6-binding proteins with antagonistic activity, and which preferably are capable of: suppressing tumor growth, e.g. in a tumor cell in which endogenous E6-BP is misexpressed; suppressing growth of papillomavirus-infected cells, e.g. HPV-infected cells; blocking or inducing apoptosis; inhibiting growth of a papillomavirus-infected cell, e.g. an HPV-infected cell, e.g. a high-risk HPV infected cell, e.g. and HPV-16, -18, -31, or -33 infected cell, e.g. a bovine papillomavirus (BPV)-infected cell; inhibiting infection of a cell by a papillomavirus, e.g. an HPV, e.g. a high-risk HPV, e.g. and HPV-16, -18, -31, or -33, e.g. a bovine papillomavirus (BPV); inhibiting transformation of a cell by a papillomavirus, e.g. an HPV, e.g. a high-risk HPV, e.g. and HPV-16, -18, -31, or -33, e.g. a bovine papillomavirus; or inhibiting immortalization of a cell, e.g. a human cell, by a papillomavirus, e.g. an HPV, e.g. a high-risk HPV, e.g. and HPV-16, -18, -31, or -33, e.g. a bovine papillomavirus.

In a preferred embodiment, a peptide having at least one biological activity of the subject E6-BP$^{SD-16}$ polypepide may differ in amino acid sequence from the sequence in SEQ ID No: 11, but such differences result in a modified protein which functions in the same or similar manner as the native E6-binding protein or which has the same or similar characteristics of the native E6-binding protein.

In yet other preferred embodiments, E6-binding protein is a recombinant fusion protein which includes a second polypeptide portion, e.g., a second polypeptide having an amino acid sequence unrelated to a protein represented by one of SEQ ID Nos: 8–14, e.g. the second polypeptide portion is glutathione-S-transferase, e.g. the second polypeptide portion is a DNA binding domain, e.g. the second polypeptide portion is a polymerase activating domain, e.g. the fusion protein is functional in a two-hybrid assay.

Yet another aspect of the present invention concerns an immunogen comprising an E6-BP polypeptide in an immunogenic preparation, the immunogen being capable of eliciting an immune response specific for said E6-BP polypeptide; e.g. a humoral response, e.g. an antibody response; e.g. a cellular response. In preferred embodiments, the immunogen comprising an antigenic determinant, e.g. a unique determinant, from a protein represented by SEQ ID No: 11.

A still further aspect of the present invention features an antibody preparation specifically reactive with an epitope of the E6-BP immunogen.

In another aspect, the invention features a E6-BP$^{SD-22}$ polypeptide, preferably a substantially pure preparation of an E6-BP$^{SD-22}$ polypeptide, or a recombinant E6-BP$^{SD-22}$ polypeptide. In preferred embodiments: the polypeptide has biological activity, e.g., it specifically binds a papillomavirus E6 protein; the polypeptide has an amino acid sequence at least 60%, 80%, 90% or 95% homologous to the amino acid sequence in SEQ ID No: 12; the polypeptide has an amino acid sequence essentially the same as the amino acid sequence in SEQ ID No: 12; the polypeptide is at least 5, 10, 20, 50, 100, or 150 amino acids in length; the polypeptide comprises at least 5, preferably at least 10, more preferably at least 20, more preferably at least 50, 100, or 150 contiguous amino acids from SEQ ID No: 12; the E6-BP$^{SD-22}$ polypeptide is either, an agonist or an antagonist of a biological activity of an E6-PB, e.g., of the regulation of cell proliferation.

In preferred embodiments the invention includes E6-binding proteins with antagonistic activity, and which preferably are capable of: suppressing tumor growth, e.g. in a tumor cell in which endogenous E6-BP is misexpressed; suppressing growth of papillomavirus-infected cells, e.g. HPV-infected cells; blocking or inducing apoptosis: inhibiting growth of a papillomavirus-infected cell, e.g. an HPV-infected cell, e.g. a high-risk HPV infected cell, e.g. and HPV-16, -18, -31, or -33 infected cell, e.g. a bovine papillomavirus (BPV)-infected cell; inhibiting infection of a cell by a papillomavirus, e.g. an HPV, e.g. a high-risk HPV, e.g. and HPV-16, -18, -31, or -33, e.g. a bovine papillomavirus (BPV); inhibiting transformation of a cell by a papillomavirus, e.g. an HPV, e.g. a high-risk HPV, e.g. and HPV-16, -18, -31, or -33, e.g. a bovine papillomavirus; or inhibiting immortalization of a cell, e.g. a human cell, by a papillomavirus, e.g. an HPV, e.g. a high-risk HPV, e.g. and HPV-16, -18, -31, or -33, e.g. a bovine papillomavirus.

In a preferred embodiment, a peptide having at least one biological activity of the subject E6-BP$^{SD-22}$ polypepide may differ in amino acid sequence from the sequence in SEQ ID No: 12, but such differences result in a modified protein which functions in the same or similar manner as the native E6-binding protein or which has the same or similar characteristics of the native E6-binding protein.

In yet other preferred embodiments, E6-binding protein is a recombinant fusion protein which includes a second polypeptide portion, e.g., a second polypeptide having an amino acid sequence unrelated to a protein represented by one of SEQ ID Nos: 8–14, e.g. the second polypeptide portion is glutathione-S-transferase, e.g. the second polypeptide portion is a DNA binding domain, e.g. the second polypeptide portion is a polymerase activating domain, e.g. the fusion protein is functional in a two-hybrid assay.

Yet another aspect of the present invention concerns an immunogen comprising an E6-BP polypeptide in an immunogenic preparation, the immunogen being capable of eliciting an immune response specific for said E6-BP polypeptide; e.g. a humoral response, e.g. an antibody response; e.g. a cellular response. In preferred embodiments, the immunogen comprising an antigenic determinant, e.g. a unique determinant, from a protein represented by SEQ ID No: 12.

A still further aspect of the present invention features an antibody preparation specifically reactive with an epitope of the E6-BP immunogen.

In another aspect, the invention features a E6-BP$^{SD-28}$ polypeptide, preferably a substantially pure preparation of an E6-BP$^{SD-28}$ polypeptide, or a recombinant E6-BP$^{SD-28}$ polypeptide. In preferred embodiments: the polypeptide has biological activity, e.g., it specifically binds a papillomavirus E6 protein; the polypeptide has an amino acid sequence at least 60%, 80%, 90% or 95% homologous to the amino acid sequence in SEQ ID No: 13; the polypeptide has an amino acid sequence essentially the same as the amino acid sequence in SEQ ID No: 13; the polypeptide is at least 5, 10, 20, 50, 100, or 150 amino acids in length; the polypeptide comprises at least 5, preferably at least 10, more preferably at least 20, more preferably at least 50, 100, or 150 contiguous amino acids from SEQ ID No: 13; the E6-BP$^{SD-28}$ polypeptide is either, an agonist or an antagonist of a biological activity of an E6-PB, e.g., of the regulation of cell proliferation.

In preferred embodiments the invention includes E6-binding proteins with antagonistic activity, and which preferably are capable of: suppressing tumor growth, e.g. in a tumor cell in which endogenous E6-BP is misexpressed; suppressing growth of papillomavirus-infected cells, e.g. HPV-infected cells; blocking or inducing apoptosis; inhibiting growth of a papillomavirus-infected cell, e.g. an HPV-infected cell, e.g. a high-risk HPV infected cell, e.g. and HPV-16, -18, -31, or -33 infected cell, e.g. a bovine papillomavirus (BPV)-infected cell; inhibiting infection of a cell by a papillomavirus, e.g. an HPV, e.g. a high-risk HPV, e.g. and HPV-16, -18, -31, or -33, e.g. a bovine papillomavirus (BPV); inhibiting transformation of a cell by a papillomavirus, e.g. an HPV, e.g. a high-risk HPV, e.g. and HPV-16, -18, -31, or -33, e.g. a bovine papillomavirus; or inhibiting immortalization of a cell, e.g. a human cell, by a papillomavirus, e.g. an HPV, e.g. a high-risk HPV, e.g. and HPV-16, -18, -31, or -33, e.g. a bovine papillomavirus.

In a preferred embodiment, a peptide having at least one biological activity of the subject E6-BP$^{SD-28}$ polypepide may differ in amino acid sequence from the sequence in SEQ ID No: 13, but such differences result in a modified protein which functions in the same or similar manner as the native E6-binding protein or which has the same or similar characteristics of the native E6-binding protein.

In yet other preferred embodiments, E6-binding protein is a recombinant fusion protein which includes a second polypeptide portion, e.g., a second polypeptide having an amino acid sequence unrelated to a protein represented by one of SEQ ID Nos: 8–14, e.g. the second polypeptide portion is glutathione-S-transferase, e.g. the second polypeptide portion is a DNA binding domain, e.g. the second polypeptide portion is a polymerase activating domain, e.g. the fusion protein is functional in a two-hybrid assay.

Yet another aspect of the present invention concerns an immunogen comprising an E6-BP polypeptide in an immunogenic preparation, the immunogen being capable of eliciting an immune response specific for said E6-BP polypeptide; e.g. a humoral response, e.g. an antibody response; e.g. a cellular response. In preferred embodiments, the immunogen comprising an antigenic determinant, e.g. a unique determinant, from a protein represented by SEQ ID No: 13.

A still further aspect of the present invention features an antibody preparation specifically reactive with an epitope of the E6-BP immunogen.

In another aspect, the invention features a E6-BP$^{SD-32}$ polypeptide, preferably a substantially pure preparation of an E6-BP$^{SD-32}$ polypeptide, or a recombinant E6-BP$^{SD-32}$ polypeptide. In preferred embodiments: the polypeptide has biological activity, e.g., it specifically binds a papillomavirus E6 protein; the polypeptide has an amino acid sequence at least 60%, 80%, 90% or 95% homologous to the amino acid sequence in SEQ ID No: 14; the polypeptide has an amino acid sequence essentially the same as the amino acid sequence in SEQ ID No: 14; the polypeptide is at least 5, 10, 20, 50, 100, or 150 amino acids in length; the polypeptide comprises at least 5, preferably at least 10, more preferably at least 20, more preferably at least 50, 100, or 150 contiguous amino acids from SEQ ID No: 14; the E6-BP$^{SD-32}$ polypeptide is either, an agonist or an antagonist of a biological activity of an E6-PB, e.g., of the regulation of cell proliferation.

In preferred embodiments the invention includes E6-binding proteins with antagonistic activity, and which preferably are capable of: suppressing tumor growth, e.g. in a tumor cell in which endogenous E6-BP is misexpressed; suppressing growth of papillomavirus-infected cells, e.g. HPV-infected cells; blocking or inducing apoptosis; inhibiting growth of a papillomavirus-infected cell, e.g. an HPV-infected cell, e.g. a high-risk HPV infected cell, e.g. and HPV-16, -18, -31, or -33 infected cell, e.g. a bovine papillomavirus (BPV)-infected cell; inhibiting infection of a cell by a papillomavirus, e.g. an HPV, e.g. a high-risk HPV, e.g. and HPV-16, -18, -31, or -33, e.g. a bovine papillomavirus (BPV); inhibiting transformation of a cell by a papillomavirus, e.g. an HPV, e.g. a high-risk HPV, e.g. and HPV-16, -18, -31, or -33, e.g. a bovine papillomavirus; or inhibiting immortalization of a cell, e.g. a human cell, by a papillomavirus, e.g. an HPV, e.g. a high-risk HPV, e.g. and HPV-16, -18, -31, or -33, e.g. a bovine papillomavirus.

In a preferred embodiment, a peptide having at least one biological activity of the subject E6-BP$^{SD-32}$ polypepide may differ in amino acid sequence from the sequence in SEQ ID No: 14, but such differences result in a modified protein which functions in the same or similar manner as the native E6-binding protein or which has the same or similar characteristics of the native E6-binding protein.

In yet other preferred embodiments, E6-binding protein is a recombinant fusion protein which includes a second polypeptide portion, e.g., a second polypeptide having an amino acid sequence unrelated to a protein represented by one of SEQ ID Nos: 8–14, e.g. the second polypeptide portion is glutathione-S-transferase, e.g. the second polypeptide portion is a DNA binding domain, e.g. the second polypeptide portion is a polymerase activating domain, e.g. the fusion protein is functional in a two-hybrid assay.

Yet another aspect of the present invention concerns an immunogen comprising an E6-BP polypeptide in an immunogenic preparation, the immunogen being capable of eliciting an immune response specific for said E6-BP polypeptide; e.g. a humoral response, e.g. an antibody response; e.g. a cellular response. In preferred embodiments, the immunogen comprising an antigenic determinant, e.g. a unique determinant, from a protein represented by SEQ ID No: 14.

A still further aspect of the present invention features an antibody preparation specifically reactive with an epitope of the E6-BP immunogen.

Another aspect of the present invention provides a substantially pure nucleic acid having a nucleotide sequence which encodes an E6-BP$^{SD-7}$ polypeptide. In preferred embodiments: the encoded polypeptide has biological activity, e.g., it specifically binds a papillomavirus E6 protein; the encoded polypeptide has an amino acid sequence at least 60%, 80%, 90% or 95% homologous to the amino acid sequence in SEQ ID No: 8; the encoded polypeptide has an amino acid sequence essentially the same as the amino acid sequence in SEQ ID No: 8; the encoded polypeptide is at least 5, 10, 20, 50, 100, or 150 amino acids length; the encoded polypeptide comprises at least 5, preferably at least 10, more preferably at least 20, more preferably at least 50, 100, or 150 contiguous amino acids from SEQ ID No: 8; the encoded E6-BP$^{SD-7}$ polypeptide is either, an agonist or an antagonist of a biological activity of an E6-PB, e.g., of the regulation of cell proliferation.

In preferred embodiments the encoded polypeptide has antagonistic activity, and is preferably capable of: suppressing tumor growth, e.g. in a tumor cell in which endogenous E6-BP is misexpressed; suppressing growth of papillomavirus-infected cells, e.g. HPV-infected cells; blocking or inducing apoptosis; inhibiting growth of a papillomavirus-infected cell, e.g. an HPV-infected cell, e.g. a high-risk HPV infected cell, e.g. and HPV-16, -18, -31, or -33 infected cell, e.g. a bovine papillomavirus (BPV)-infected cell; inhibiting infection of a cell by a papillomavirus, e.g. an HPV, e.g. a high-risk HPV, e.g. and HPV-16, -18, -31, or -33, e.g. a bovine papillomavirus (BPV); inhibiting transformation of a cell by a papillomavirus, e.g. an HPV, e.g. a high-risk HPV, e.g. and HPV-16, -18, -31, or -33, e.g. a bovine papillomavirus; or inhibiting immortalization of a cell, e.g. a human cell, by a papillomavirus, e.g. an HPV, e.g. a high-risk HPV, e.g. and HPV-16, -18, -31, or -33, e.g. a bovine papillomavirus.

In a preferred embodiment, the encoded peptide having at least one biological activity of the subject E6-BP$^{SD-7}$ polypepide may differ in amino acid sequence from the sequence in SEQ ID No: 8, but such differences result in a modified protein which functions in the same or similar manner as the native E6-binding protein or which has the same or similar characteristics of the native E6-binding protein.

In yet other preferred embodiments,the encoded polypeptide is a recombinant fusion protein which includes a second polypeptide portion, e.g., a second polypeptide having an amino acid sequence unrelated to a protein represented by one of SEQ ID Nos: 8–14, e.g. the second polypeptide portion is glutathione-S-transferase, e.g. the second polypeptide portion is a DNA binding domain, e.g. the second polypeptide portion is a polymerase activating domain, e.g. the fusion protein is functional in a two-hybrid assay.

Furthermore, in certain preferred embodiments, the subject E6-BP$^{SD-7}$ nucleic acid will include a transcriptional regulatory sequence, e.g. at least one of a transcriptional promoter or transcriptional enhancer sequence, operably linked to the E6-BP$^{SD-7}$ gene sequence, e.g., to render the E6-BP$^{SD-7}$ gene sequence suitable for use as an expression vector.

In yet a further preferred embodiment, the nucleic acid which encodes an E6-BP$^{SD-7}$ polypeptide of the invention, which hybridizes under stringent conditions to a nucleic acid probe corresponding to at least 12 consecutive nucleotides of SEQ ID No: 1; more preferably to at least 20 consecutive nucleotides of SEQ ID No: 1; more preferably to at least 40 consecutive nucleotides of SEQ ID No: 1. In yet a further preferred embodiment, the E6-BP encoding nucleic acid hybridizes to a nucleic acid probe corresponding to a sub-sequence encoding at least 4 consecutive amino acids, more preferably at least 10 consecutive amino acid residues, and even more preferably at least 20 amino acid residues between residues 1 and 133 of SEQ ID No: 8.

In preferred embodiments: the nucleic acid sequence includes at least 1, 2, 3 or 5, and preferably at least 10, 20, 50, or 100 nucleotides from the region of SEQ ID No: 1 which encodes amino acid residues 1–133 of SEQ ID No: 8; the encoded peptide includes at least 1, 2, 3, 5, 10, 20, or 30 amino acid residues from amino acid residues 1–133 of SEQ ID No: 8; the nucleic acid sequence is other than nucleotide residues 572–875 of SEQ ID No: 1, e.g., it is longer, shorter, has a different 3' end or a different 5' end.

Another aspect of the present invention provides a substantially pure nucleic acid having a nucleotide sequence which encodes an E6-BP$^{SD-8}$ polypeptide. In preferred embodiments: the encoded polypeptide has biological activity, e.g., it specifically binds a papillomavirus E6 protein; the encoded polypeptide has an amino acid sequence at least 60%, 80%, 90% or 95% homologous to the amino acid sequence in SEQ ID No: 9; the encoded polypeptide has an amino acid sequence essentially the same as the amino acid sequence in SEQ ID No: 9; the encoded polypeptide is at least 5, 10, 20, 50, 100, or 150 amino acids in length; the encoded polypeptide comprises at least 5, preferably at least 10, more preferably at least 20, more preferably at least 50, 100, or 150 contiguous amino acids from SEQ ID No: 9; the encoded E6-BP$^{SD-8}$ polypeptide is either, an agonist or an antagonist of a biological activity of an E6-PB, e.g., of the regulation of cell proliferation.

In preferred embodiments the encoded polypeptide has antagonistic activity, and is preferably capable of: suppressing tumor growth, e.g. in a tumor cell in which endogenous E6-BP is misexpressed; suppressing growth of papillomavirus-infected cells, e.g. HPV-infected cells; blocking or inducing apoptosis; inhibiting growth of a papillomavirus-infected cell, e.g. an HPV-infected cell, e.g. a high-risk HPV infected cell, e.g. and HPV-16, -18, -31, or -33 infected cell, e.g. a bovine papillomavirus (BPV)-infected cell; inhibiting infection of a cell by a papillomavirus, e.g. an HPV, e.g. a high-risk HPV, e.g. and HPV-16, -18, -31, or -33, e.g. a bovine papillomavirus (BPV); inhibiting transformation of a cell by a papillomavirus, e.g. an HPV, e.g. a high-risk HPV, e.g. and HPV-16, -18, -31, or -33, e.g. a bovine papillomavirus; or inhibiting immortalization of a cell, e.g. a human cell, by a papillomavirus, e.g. an HPV, e.g. a high-risk HPV, e.g. and HPV-16, -18, -31, or -33, e.g. a bovine papillomavirus.

In a preferred embodiment, the encoded peptide having at least one biological activity of the subject E6-BP$^{SD-8}$ polypepide may differ in amino acid sequence from the sequence in SEQ ID No: 9, but such differences result in a modified protein which functions in the same or similar manner as the native E6-binding protein or which has the same or similar characteristics of the native E6-binding protein.

In yet other preferred embodiments,the encoded polypeptide is a recombinant fusion protein which includes a second polypeptide portion, e.g., a second polypeptide having an amino acid sequence unrelated to a protein represented by one of SEQ ID Nos: 8–14, e.g. the second polypeptide portion is glutathione-S-transferase, e.g. the second polypeptide portion is a DNA binding domain, e.g. the second polypeptide portion is a polymerase activating domain, e.g. the fusion protein is functional in a two-hybrid assay.

Furthermore, in certain preferred embodiments, the subject E6-BP$^{SD-8}$ nucleic acid will include a transcriptional regulatory sequence, e.g. at least one of a transcriptional promoter or transcriptional enhancer sequence, operably linked to the E6-BP$^{SD-8}$ gene sequence, e.g., to render the E6-BP$^{SD-8}$ gene sequence suitable for use as an expression vector.

In yet a further preferred embodiment, the nucleic acid which encodes an E6-BP polypeptide of the invention, which hybridizes under stringent conditions to a nucleic acid probe corresponding to at least 12 consecutive nucleotides of SEQ ID No: 2; more preferably to at least 20 consecutive nucleotides of SEQ ID No: 2; more preferably to at least 40 consecutive nucleotides of SEQ ID No: 2.

Another aspect of the present invention provides a substantially pure nucleic acid having a nucleotide sequence which encodes an E6-BP$^{SD-12}$ polypeptide. In preferred embodiments: the encoded polypeptide has biological activity, e.g., it specifically binds a papillomavirus E6 protein; the encoded polypeptide has an amino acid sequence at least 60%, 80%, 90% or 95% homologous to the amino acid sequence in SEQ ID No: 10; the encoded polypeptide has an amino acid sequence essentially the same as the amino acid sequence in SEQ ID No: 10; the encoded polypeptide is at least 5, 10, 20, 50, 100, or 150 amino acids in length; the encoded polypeptide comprises at least 5, preferably at least 10, more preferably at least 20, more preferably at least 50, 100, or 150 contiguous amino acids from SEQ ID No: 10; the encoded E6-BP$^{SD-12}$ polypeptide is either, an agonist or an antagonist of a biological activity of an E6-PB, e.g., of the regulation of cell proliferation.

In preferred embodiments the encoded polypeptide has antagonistic activity, and is preferably capable of: suppressing tumor growth, e.g. in a tumor cell in which endogenous E6-BP is misexpressed; suppressing growth of papillomavirus-infected cells, e.g. HPV-infected cells; blocking or inducing apoptosis; inhibiting growth of a papillomavirus-infected cell, e.g. an HPV-infected cell, e.g. a high-risk HPV infected cell, e.g. and HPV-16, -18, -31, or -33 infected cell, e.g. a bovine papillomavirus (BPV)-infected cell; inhibiting infection of a cell by a papillomavirus, e.g. an HPV, e.g. a high-risk HPV, e.g. and HPV-16, -18, -31, or -33, e.g. a bovine papillomavirus (BPV); inhibiting transformation of a cell by a papillomavirus, e.g. an HPV, e.g. a high-risk HPV, e.g. and HPV-16, -18, -31, or -33, e.g. a bovine papillomavirus; or inhibiting immortalization of a cell, e.g. a human cell, by a papillomavirus, e.g. an HPV, e.g. a high-risk HPV, e.g. and HPV-16, -18, -31, or -33, e.g. a bovine papillomavirus.

In a preferred embodiment, the encoded peptide having at least one biological activity of the subject E6-BP$^{SD-12}$ polypepide may differ in amino acid sequence from the sequence in SEQ ID No: 10, but such differences result in a modified protein which functions in the same or similar manner as the native E6-binding protein or which has the same or similar characteristics of the native E6-binding protein.

In yet other preferred embodiments,the encoded polypeptide is a recombinant fusion protein which includes a second polypeptide portion, e.g., a second polypeptide having an amino acid sequence unrelated to a protein represented by one of SEQ ID Nos: 8–14, e.g. the second polypeptide portion is glutathione-S-transferase, e.g. the second polypeptide portion is a DNA binding domain, e.g. the second polypeptide portion is a polymerase activating domain, e.g. the fusion protein is functional in a two-hybrid assay.

Furthermore, in certain preferred embodiments, the subject E6-BP$^{SD-12}$ nucleic acid will include a transcriptional regulatory sequence, e.g. at least one of a transcriptional promoter or transcriptional enhancer sequence, operably linked to the E6-BP$^{SD-12}$ gene sequence, e.g., to render the E6-BP$^{SD-12}$ gene sequence suitable for use as an expression vector.

In yet a further preferred embodiment, the nucleic acid which encodes an E6-BP polypeptide of the invention, which hybridizes under stringent conditions to a nucleic acid probe corresponding to at least 12 consecutive nucleotides of SEQ ID No: 3; more preferably to at least 20 consecutive nucleotides of SEQ ID No: 3; more preferably to at least 40 consecutive nucleotides of SEQ ID No: 3.

Another aspect of the present invention provides a substantially pure nucleic acid having a nucleotide sequence which encodes an E6-BP$^{SD-16}$ polypeptide. In preferred embodiments: the encoded polypeptide has biological activity, e.g., it specifically binds a papillomavirus E6 protein; the encoded polypeptide has an amino acid sequence at least 60%, 80%, 90% or 95% homologous to the amino acid sequence in SEQ ID No: 11; the encoded polypeptide has an amino acid sequence essentially the same as the amino acid sequence in SEQ ID No: 11; the encoded polypeptide is at least 5, 10, 20, 50, 100, or 150 amino acids in length; the encoded polypeptide comprises at least 5, preferably at least 10, more preferably at least 20, more preferably at least 50, 100, or 150 contiguous amino acids from SEQ ID No: 11; the encoded E6-BP$^{SD-16}$ polypeptide is either, an agonist or an antagonist of a biological activity of an E6-PB, e.g., of the regulation of cell proliferation.

In preferred embodiments the encoded polypeptide has antagonistic activity, and is preferably capable of: suppressing tumor growth, e.g. in a tumor cell in which endogenous E6-BP is misexpressed; suppressing growth of papillomavirus-infected cells, e.g. HPV-infected cells; blocking or inducing apoptosis; inhibiting growth of a papillomavirus-infected cell, e.g. an HPV-infected cell, e.g. a high-risk HPV infected cell, e.g. and HPV-16, -18, -31, or -33 infected cell, e.g. a bovine papillomavirus (BPV)-infected cell; inhibiting infection of a cell by a papillomavirus, e.g. an HPV, e.g. a high-risk HPV, e.g. and HPV-16, -18, -31, or -33, e.g. a bovine papillomavirus (BPV); inhibiting transformation of a cell by a papillomavirus, e.g. an HPV, e.g. a high-risk HPV, e.g. and HPV-16, -18, -31, or -33, e.g. a bovine papillomavirus; or inhibiting immortalization of a cell, e.g. a human cell, by a papillomavirus, e.g. an HPV, e.g. a high-risk HPV, e.g. and HPV-16, -18, -31, or -33, e.g. a bovine papillomavirus.

In a preferred embodiment, the encoded peptide having at least one biological activity of the subject E6-BP$^{SD-16}$ polypepide may differ in amino acid sequence from the sequence in SEQ ID No: 11, but such differences result in a modified protein which functions in the same or similar manner as the native E6-binding protein or which has the same or similar characteristics of the native E6-binding protein.

In yet other preferred embodiments,the encoded polypeptide is a recombinant fusion protein which includes a second polypeptide portion, e.g., a second polypeptide having an amino acid sequence unrelated to a protein represented by one of SEQ ID Nos: 8–14, e.g. the second polypeptide portion is glutathione-S-transferase, e.g. the second polypeptide portion is a DNA binding domain, e.g. the second polypeptide portion is a polymerase activating domain, e.g. the fusion protein is functional in a two-hybrid assay.

Furthermore, in certain preferred embodiments, the subject E6-BP$^{SD-16}$ nucleic acid will include a transcriptional regulatory sequence, e.g., at least one of a transcriptional promoter or transcriptional enhancer sequence, operably linked to the E6-BP$^{SD-16}$ gene sequence, e.g., to render the E6-BP$^{SD-16}$ gene sequence suitable for use as an expression vector.

In yet a further preferred embodiment, the nucleic acid which encodes an E6-BP polypeptide of the invention, which hybridizes under stringent conditions to a nucleic acid probe corresponding to at least 12 consecutive nucleotides of SEQ ID No: 4; more preferably to at least 20 consecutive nucleotides of SEQ ID No: 4; more preferably to at least 40 consecutive nucleotides of SEQ ID No: 4.

Another aspect of the present invention provides a substantially pure nucleic acid having a nucleotide sequence which encodes an E6-BP$^{SD-22}$ polypeptide. In preferred embodiments: the encoded polypeptide has biological activity, e.g., it specifically binds a papillomavirus E6 protein; the encoded polypeptide has an amino acid sequence at least 60%, 80%, 90% or 95% homologous to the amino acid sequence in SEQ ID No: 12; the encoded polypeptide has an amino acid sequence essentially the same as the amino acid sequence in SEQ ID No: 12; the encoded polypeptide is at least 5, 10, 20, 50, 100, or 150 amino acids in length; the encoded polypeptide comprises at least 5, preferably at least 10, more preferably at least 20, more preferably at least 50, 100, or 150 contiguous amino acids from SEQ ID No: 12; the encoded E6-BP$^{SD-22}$ polypeptide is either, an agonist or an antagonist of a biological activity of an E6-PB, e.g., of the regulation of cell proliferation.

In preferred embodiments the encoded polypeptide has antagonistic activity, and is preferably capable of: suppressing tumor growth, e.g. in a tumor cell in which endogenous E6-BP is misexpressed; suppressing growth of papillomavirus-infected cells, e.g. HPV-infected cells; blocking or inducing apoptosis; inhibiting growth of a papillomavirus-infected cell, e.g. an HPV-infected cell, e.g. a high-risk HPV infected cell, e.g. and HPV-16, -18, -31, or -33 infected cell, e.g. a bovine papillomavirus (BPV)-infected cell; inhibiting infection of a cell by a papillomavirus, e.g. an HPV, e.g. a high-risk HPV, e.g. and HPV-16, -18, -31, or -33, e.g. a bovine papillomavirus (BPV); inhibiting transformation of a cell by a papillomavirus, e.g. an HPV, e.g. a high-risk HPV, e.g. and HPV-16, -18, -31, or -33, e.g. a bovine papillomavirus; or inhibiting immortalization of a cell, e.g. a human cell, by a papillomavirus, e.g. an HPV, e.g. a high-risk HPV, e.g. and HPV-16, -18, -31, or -33, e.g. a bovine papillomavirus.

In a preferred embodiment, the encoded peptide having at least one biological activity of the subject E6-BP$^{SD-22}$ polypepide may differ in amino acid sequence from the sequence in SEQ ID No: 12, but such differences result in a modified protein which functions in the same or similar manner as the native E6-binding protein or which has the same or similar characteristics of the native E6-binding protein.

In yet other preferred embodiments,the encoded polypeptide is a recombinant fusion protein which includes a second polypeptide portion, e.g., a second polypeptide having an amino acid sequence unrelated to a protein represented by one of SEQ ID Nos: 8–14, e.g. the second polypeptide portion is glutathione-S-transferase, e.g. the second polypeptide portion is a DNA binding domain, e.g. the second polypeptide portion is a polymerase activating domain, e.g. the fusion protein is functional in a two-hybrid assay.

Furthermore, in certain preferred embodiments, the subject E6-BP$^{SD-22}$ nucleic acid will include a transcriptional regulatory sequence, e.g. at least one of a transcriptional promoter or transcriptional enhancer sequence, operably linked to the E6-BP$^{SD-22}$ gene sequence, e.g., to render the E6-BP$^{SD-22}$ gene sequence suitable for use as an expression vector.

In yet a further preferred embodiment, the nucleic acid which encodes an E6-BP polypeptide of the invention, which hybridizes under stringent conditions to a nucleic acid probe corresponding to at least 12 consecutive nucleotides of SEQ ID No: 5; more preferably to at least 20 consecutive nucleotides of SEQ ID No: 5; more preferably to at least 40 consecutive nucleotides of SEQ ID No: 5.

Another aspect of the present invention provides a substantially pure nucleic acid having a nucleotide sequence which encodes an E6-BP$^{SD-28}$ polypeptide. In preferred embodiments: the encoded polypeptide has biological activity, e.g., it specifically binds a papillomavirus E6 protein; the encoded polypeptide has an amino acid sequence at least 60%, 80%, 90% or 95% homologous to the amino acid sequence in SEQ ID No: 13; the encoded polypeptide has an amino acid sequence essentially the same as the amino acid sequence in SEQ ID No: 13; the encoded polypeptide is at least 5, 10, 20, 50, 100, or 150 amino acids in length; the encoded polypeptide comprises at least 5, preferably at least 10, more preferably at least 20, more preferably at least 50, 100, or 150 contiguous amino acids from SEQ ID No: 13; the encoded E6-BP$^{SD-28}$ polypeptide is either, an agonist or an antagonist of a biological activity of an E6-PB, e.g., of the regulation of cell proliferation.

In preferred embodiments the encoded polypeptide has antagonistic activity, and is preferably capable of: suppressing tumor growth, e.g. in a tumor cell in which endogenous E6-BP is misexpressed; suppressing growth of papillomavirus-infected cells, e.g. HPV-infected cells; blocking or inducing apoptosis; inhibiting growth of a papillomavirus-infected cell, e.g. an HPV-infected cell, e.g. a high-risk HPV infected cell, e.g. and HPV-16, -18, -31, or -33 infected cell, e.g. a bovine papillomavirus (BPV)-infected cell; inhibiting infection of a cell by a papillomavirus, e.g. an HPV, e.g. a high-risk HPV, e.g. and HPV-16, -18, -31, or -33, e.g. a bovine papillomavirus (BPV); inhibiting transformation of a cell by a papillomavirus, e.g. an HPV, e.g. a high-risk HPV, e.g. and HPV-16, -18, -31, or -33, e.g. a bovine papillomavirus; or inhibiting immortalization of a cell, e.g. a human cell, by a papillomavirus, e.g. an HPV, e.g. a high-risk HPV, e.g. and HPV-16, -18, -31, or -33, e.g. a bovine papillomavirus.

In a preferred embodiment, the encoded peptide having at least one biological activity of the subject E6-BP$^{SD-28}$ polypepide may differ in amino acid sequence from the sequence in SEQ ID No: 13, but such differences result in a modified protein which functions in the same or similar manner as the native E6-binding protein or which has the same or similar characteristics of the native E6-binding protein.

In yet other preferred embodiments, the encoded polypeptide is a recombinant fusion protein which includes a second polypeptide portion, e.g., a second polypeptide having an amino acid sequence unrelated to a protein represented by one of SEQ ID Nos: 8–14, e.g. the second polypeptide portion is glutathione-S-transferase, e.g. the second polypeptide portion is a DNA binding domain, e.g. the second polypeptide portion is a polymerase activating domain, e.g. the fusion protein is functional in a two-hybrid assay.

Furthermore, in certain preferred embodiments, the subject E6-BP$^{SD-28}$ nucleic acid will include a transcriptional regulatory sequence, e.g. at least one of a transcriptional promoter or transcriptional enhancer sequence, operably linked to the E6-BP$^{SD-28}$ gene sequence, e.g., to render the E6-BP$^{SD-28}$ gene sequence suitable for use as an expression vector.

In yet a further preferred embodiment, the nucleic acid which encodes an E6-BP polypeptide of the invention, which hybridizes under stringent conditions to a nucleic acid probe corresponding to at least 12 consecutive nucleotides of SEQ ID No: 6; more preferably to at least 20 consecutive nucleotides of SEQ ID No: 6; more preferably to at least 40 consecutive nucleotides of SEQ ID No: 6.

Another aspect of the present invention provides a substantially pure nucleic acid having a nucleotide sequence which encodes an E6-BP$^{SD-32}$ polypeptide. In preferred embodiments: the encoded polypeptide has biological activity, e.g., it specifically binds a papillomavirus E6 protein; the encoded polypeptide has an amino acid sequence at least 60%, 80%, 90% or 95% homologous to the amino acid sequence in SEQ ID No: 14; the encoded polypeptide has an amino acid sequence essentially the same as the amino acid sequence in SEQ ID No: 14; the encoded polypeptide is at least 5, 10, 20, 50, 100, or 150 amino acids in length; the encoded polypeptide comprises at least 5, preferably at least 10, more preferably at least 20, more preferably at least 50, 100, or 150 contiguous amino acids from SEQ ID No: 14; the encoded E6-BP$^{SD-32}$ polypeptide is either, an agonist or an antagonist of a biological activity of an E6-PB, e.g., of the regulation of cell proliferation.

In preferred embodiments the encoded polypeptide has antagonistic activity, and is preferably capable of: suppressing tumor growth., e.g. in a tumor cell in which endogenous E6-BP is misexpressed; suppressing growth of papillomavirus-infected cells, e.g. HPV-infected cells; blocking or inducing apoptosis; inhibiting growth of a papillomavirus-infected cell, e.g. an HPV-infected cell, e.g. a high-risk HPV infected cell, e.g. and HPV-16, -18, -31, or -33 infected cell, e.g. a bovine papillomavirus (BPV)-infected cell; inhibiting infection of a cell by a papillomavirus, e.g. an HPV, e.g. a high-risk HPV, e.g. and HPV-16, -18, -31, or -33, e.g. a bovine papillomavirus (BPV); inhibiting transformation of a cell by a papillomavirus, e.g. an HPV, e.g. a high-risk HPV, e.g. and HPV-16, -18, -31, or -33, e.g. a bovine papillomavirus; or inhibiting immortalization of a cell, e.g. a human cell, by a papillomavirus, e.g. an HPV, e.g. a high-risk HPV, e.g. and HPV-16, -18, -31, or -33, e.g. a bovine papillomavirus.

In a preferred embodiment, the encoded peptide having at least one biological activity of the subject E6-BP$^{SD-32}$ polypepide may differ in amino acid sequence from the sequence in SEQ ID No: 14, but such differences result in a modified protein which functions in the same or similar manner as the native E6-binding protein or which has the same or similar characteristics of the native E6-binding protein.

In yet other preferred embodiments, the encoded polypeptide is a recombinant fusion protein which includes a second polypeptide portion, e.g., a second polypeptide having an amino acid sequence unrelated to a protein represented by one of SEQ ID Nos: 8–14, e.g. the second polypeptide portion is glutathione-S-transferase, e.g. the second polypeptide portion is a DNA binding domain, e.g. the second polypeptide portion is a polymerase activating domain, e.g. the fusion protein is functional in a two-hybrid assay.

Furthermore, in certain preferred embodiments, the subject E6-BP$^{SD-32}$ nucleic acid will include a transcriptional regulatory sequence, e.g. at least one of a transcriptional promoter or transcriptional enhancer sequence, operably linked to the E6-BP$^{SD-32}$ gene sequence, e.g., to render the E6-BP$^{SD-32}$ gene sequence suitable for use as an expression vector.

In yet a further preferred embodiment, the nucleic acid which encodes an E6-BP polypeptide of the invention, which hybridizes under stringent conditions to a nucleic acid probe corresponding to at least 12 consecutive nucleotides of SEQ ID No: 7; more preferably to at least 20 consecutive nucleotides of SEQ ID No: 7; more preferably to at least 40 consecutive nucleotides of SEQ ID No: 7.

The invention also features transgenic non-human animals, e.g. mice, rats, rabbits or pigs, having a transgene, e.g., animals which include (and preferably express) a heterologous form of one of the novel E6-BP genes described herein, e.g. a gene derived from humans, or a gene which misexpress an endogenous E6-BP gene, e.g., an animal which expression of one or more of the subject E6-BP's is disrupted. Such a transgenic animal can serve as an animal model for studying cellular disorders comprising mutated or mis-expressed E6-BP alleles or for use in drug screening.

The invention also provides a probe/primer comprising a substantially purified oligonucleotide, wherein the oligonucleotide comprises a region of nucleotide sequence which hybridizes under stringent conditions to at least 10 consecutive nucleotides of sense or antisense sequence of one of SEQ ID Nos: 1–7, or naturally occurring mutants thereof. In preferred embodiments, the probe/primer further includes a label group attached thereto and able to be detected. The label group can be selected, e.g., from a group consisting of radioisotopes, fluorescent compounds, enzymes, and enzyme co-factors. Probes of the invention can be used as a part of a diagnostic test kit for identifying transformed cells, such as for measuring in a sample of cells isolated from a patient, a level of a nucleic acid encoding one of the subject E6-binding proteins; e.g. measuring the E6-BP mRNA level in a cell; e.g. determining whether the genomic E6-BP gene has been mutated or deleted. Preferably the oligonucleotide is at least 10 and less than 20, 30, 50, 100, or 150 nucleotides in length.

In yet another aspect, the invention provides an assay for screening test compounds for an interaction; e.g., inhibition, of an E6-BP polypeptide with a papillomavirus E6 protein. The method includes the steps of (i) combining a viral E6 protein, an E6-BP, e.g., an E6-BP of the invention (e.g. a protein expressed from one of the clones selected from the group SD-7, SD-8, SD-12, SD-16, SD-22, SD-28 or SD-32, or keratin-17, apoferritin, a nucleophosamin, a ribonucleoportein, a proteasome subunit, a complement decay-accelerating factor), and a test compound, e.g., under conditions wherein in the absence of the test compound the E6 protein and the E6-binding protein are able to interact; and (ii) detecting the formation of a complex which includes the E6 protein and the E6-binding protein. A change, e.g., a decrease, in the formation of the complex in the presence of a test compound (relative to what is seen in the absence of the test compound) is indicative of a modulation, e.g., an inhibition, of the interaction between the E6 protein and the E6-binding protein. In preferred embodiments: the E6 protein is an HPV E6 protein, e.g. from a high-risk HPV, e.g. from HPV-16, -18, -31 or -33; the E6 protein is a BPV E6 protein; the E6 protein and the E6-binding protein are combined in a cell-free system and contacted with the test compound; i.e. the cell-free system is selected from a group consisting of a cell lysate and a reconstituted protein mixture; the E6-binding protein are simultaneously expressed in a cell, and the cell is contacted with the test compound, e.g. the E6-binding protein comprise an interaction trap assay (two hybrid assay).

The present invention also provides a method for treating an animal having unwanted cell growth characterized by a loss of wild-type function of one or more of the subject E6-binding proteins, comprising administering a therapeutically effective amount of an agent able to inhibit the interaction of the E6-binding protein with other cellular or viral proteins. In one embodiment, the method comprises administering a nucleic acid construct encoding a polypeptides represented in one of SEQ ID Nos: 8–14, under conditions wherein the construct is incorporated by cells deficient in that E6-binding protein, and under conditions wherein the recombinant gene is expressed, e.g. by gene therapy techniques.

Another aspect of the present invention provides a method of determining if a subject, e.g. a human patient, is at risk for a disorder characterized by unwanted cell proliferation. The method includes detecting, in a tissue of the subject, the presence or absence of a genetic lesion characterized by at least one of (i) a mutation of a gene encoding a protein represented by one of SEQ ID Nos: 8–14, or a homolog thereof; or (ii) the mis-expression of a gene encoding a protein represented by one of SEQ ID Nos: 8–14. In preferred embodiments: detecting the genetic lesion includes ascertaining the existence of at least one of: a deletion of one or more nucleotides from the E6-BP gene; an addition of one or more nucleotides to the gene, an substitution of one or more nucleotides of the gene, a gross chromosomal rearrangement of the gene; an alteration in the level of a messenger RNA transcript of the gene; the presence of a non-wild type splicing pattern of a messenger RNA transcript of the gene; or a non-wild type level of the protein.

For example, detecting the genetic lesion can include (i) providing a probe/primer including an oligonucleotide containing a region of nucleotide sequence which hybridizes to a sense or antisense sequence of one of SEQ ID Nos: 1–7, or naturally occurring mutants thereof or 5' or 3' flanking sequences naturally associated with the E6-BP gene; (ii) exposing the probe/primer to nucleic acid of the tissue; and (iii) detecting, by hybridization of the probe/primer to the nucleic acid, the presence or absence of the genetic lesion; e.g. wherein detecting the lesion comprises utilizing the probe/primer to determine the nucleotide sequence of the E6-BP gene and, optionally, of the flanking nucleic acid sequences; e.g. wherein detecting the lesion comprises utilizing the probe/primer in a polymerase chain reaction (PCR); e.g. wherein detecting said lesion comprises utilizing the probe/primer in a ligation chain reaction (LCR). In alternate embodiments, the level of said protein is detected in an immunoassay using an antibody which is specifically immunoreactive with, e.g. a protein represented by one of SEQ ID Nos: 8–14.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, *Molecular Cloning A Laboratory Manual,* 2nd Ed., ed. by Sambrook, Fritsch and Maniatis (Cold Spring Harbor Laboratory Press: 1989); *DNA Cloning,* Volumes I and II (D. N. Glover ed., 1985); *Oligonucleotide Synthesis* (M. J. Gait ed., 1984); Mullis et al. U.S. Pat. No: 4,683,195; *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., New York); *Gene Transfer Vectors For Mammalian Cells* (J. H. Miller and M. P. Calos eds., 1987, Cold Spring Harbor Laboratory); *Methods In Enzymology,* Vols. 154 and 155 (Wu et al. eds.), *Immunochemical Methods In Cell And Molecular Biology* (Mayer and Walker, eds., Academic Press, London, 1987); *Handbook Of Experimental Immunology,* Volumes I–IV (D. M. Weir and C. C. Blackwell, eds., 1986); *Manipulating the Mouse Embryo,* (Cold Spring Harbor Laboratory Press, Cold Spring Harbor, N.Y., 1986).

Other features and advantages of the invention will be apparent from the following detailed description, and from the claims.

DETAILED DESCRIPTION OF THE INVENTION

Figure 1:
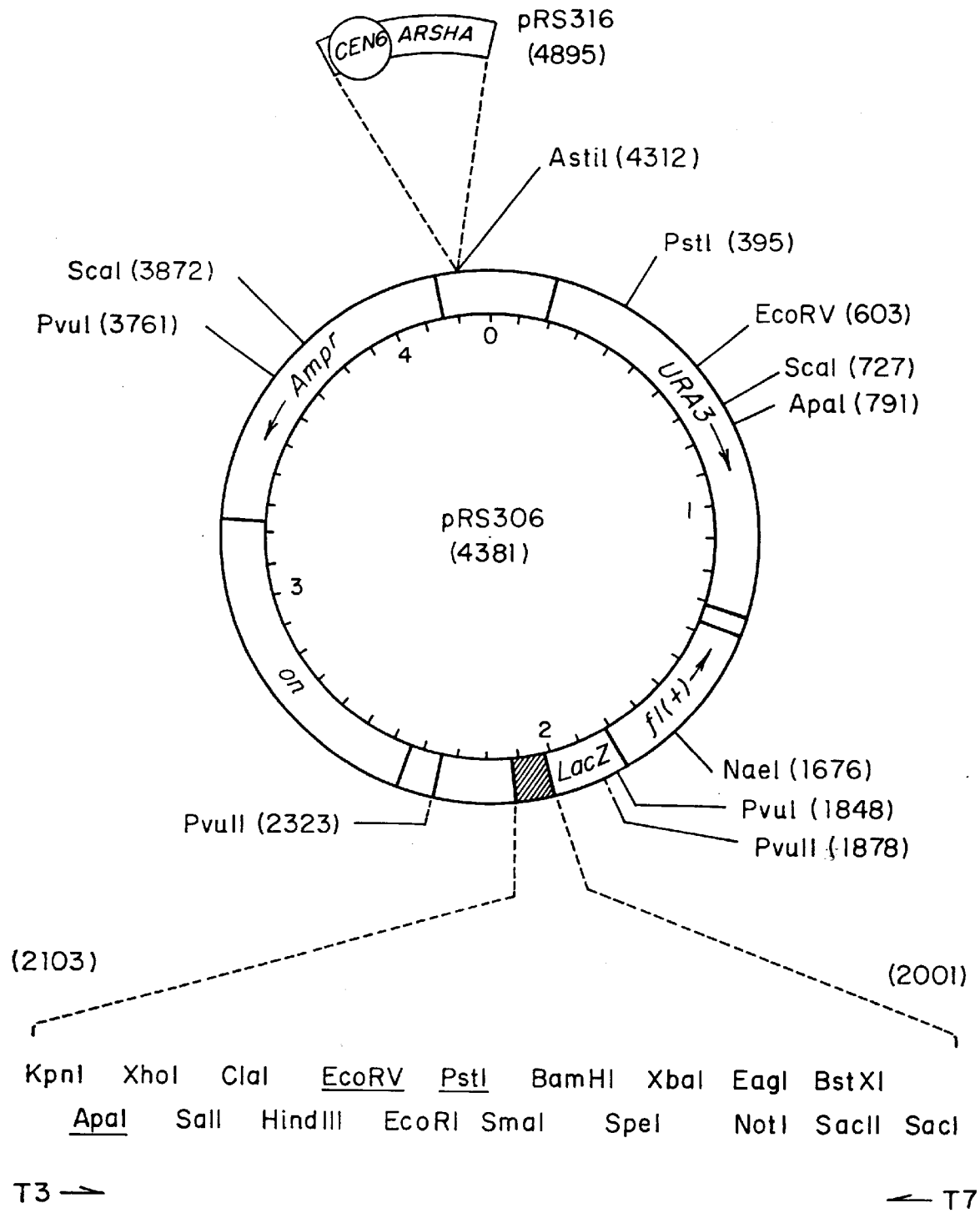
FIG. 1 is the general map of the pRS306 plasmid (Sikorski et al. (1989) *Genetics* 122:19) used to construct the VP16/cDNA fusion gene for expression in a two hybrid assay.

The papillomaviruses (PV) are infectious agents that can cause benign epithelial tumors, or warts, in their natural hosts. Of particular relevance to the field of human cancer, infection with specific human papillomaviruses (HPV) has been associated with the development of human epithelial malignancies, including that of the uterine cervix, genitalia, skin and less frequently, other sites. Two of the transforming proteins produced by papillomaviruses, the E6 protein and E7 protein, form complexes with the tumor suppressor gene products p53 and Rb, respectively, indicating that these viral proteins may exert their functions through critical pathways that regulate cellular growth control.

However, our studies of immortalization by the papillomavirus E6 protein show that while p53 binding is necessary for efficient immortalization, the E6 protein has additional properties in the establishment of an immortal state. Moreover, our findings suggest both BPV and "low risk" HPV E6 proteins have one or more functions in common with the high risk HPV E6 protein. We have adapted the two hybrid assay (U.S. Pat. No. 5,283,173) to identify other human cellular proteins which interact with the viral E6 oncoprotein and which could be candidate proteins participating in PV infectivity and/or transformation.

Starting with a yeast strain expressing the HPV-16 E6 gene fused at its C-terminus to the BPV E2 DNA-binding domain, and further containing a lacZ reporter construct driven by a promoter containing four E2 binding elements, we generated a two hybrid assay for screening human cDNA libraries. This strain was then transformed with a library of yeast shuttle vector plasmid in which randomly primed HeLa cell cDNA was inserted C-terminal to the strong VP16 transcription activation domain. Interaction of the VP16/cDNA fusion proteins with the E6/E2 hybrid protein would recruit the VP16 transcriptional activation domain to the E2 binding site and activate expression of the lacZ gene. This has led to the successful isolation of a number of human genes which encode proteins that specifically interact with E6. The invention, as described below, therefore derives, in part, from the discovery that, in addition to the tumor suppressor protein "p53" and the cellular protein "E6-AP", the papillomavirus transforming protein E6 is also associated with several other cellular proteins (hereinafter termed "cellular E6-binding proteins" or "E6-BPs"), which association is presumably important to the pathogenesis of papillomavirus infection and papillomavirus-mediated disease states. For example, association of one of the subject E6-binding proteins with E6 can result in alteration of the localization of either or both proteins, a change in the biological activity of the protein, a modification of the cellular half-life of the protein, or a combination thereof. Thus, embodiments of the invention make available diagnostic and therapeutic assays and reagents for detecting and treating papillomavirus-infected cells.

For example, each of the subject E6-BPs can be used as the basis of assays for identifying agents that alter, e.g. decrease, the ability of a particular E6-binding protein to bind a papillomavirus E6 protein and thereby, through inhibition of E6-BP/E6 complexes, inhibit papillomavirus infection, transformation and/or immortalization. Such agents can be of use therapeutically to prevent E6-BP/E6 complexes in cells infected by, for example, human papillomaviruses, e.g. HPV-1, HPV-2, HPV-3, HPV-4, HPV-5, HPV-6, HPV-7, HPV-8, HPV-9, HPV-10, HPV-11, HPV-12, HPV-14, HPV-13, HPV-15, HPV-16, HPV-17 or HPV-18, particularly high-risk HPVs, such as HPV-16, HPV-18, HPV-31 and HPV-33. Contacting such cells with agents that alter the formation of one or more E6-BP/E6 complexes can inhibit pathological progression of papillomavirus infection, such as preventing or reversing the formation of warts, e.g. Plantar warts (verruca plantaris), common warts (verruca plana), Butcher's common warts, flat warts, genital warts (condyloma acuminatum), or epidermodysplasia verruciformis; as well as treating papillomavirus cells which have become, or are at risk of becoming, transformed and/or immortalized, e.g. cancerous, e.g. a laryngeal papilloma, a focal epithelial, a cervical carcinoma.

In one embodiment, the cellular E6-binding protein is a cytokeratin, and binding of the PV E6 protein to the cytokeratin may contribute to, for example, collapse of the cytokeratin matrix, disruption of the cell envelope, disruption of the spatial organization of the infected epithelial tissue, and/or loss of focal adhesion by the PV-infected cells. In a preferred embodiment, the cytokeratin is keratin-17. Disruption of the E6/cytokeratin interaction might therefore influence infectivity of papillomavirus, e.g. by affecting release of viral particles from infected cells, as well as, by preventing PV-induced alteration of epithelial phenotype, e.g. of keratinocytes, e.g. of squamous epithelium, e.g. of stratified squamous epithelium.

In another embodiment, the cellular E6-binding protein is a nucleolar protein involved in cell proliferation, such as for example, transcriptional regulation, mRNA processing, mRNA localization, or ribosome maturation, and binding of papillomavirus E6 to the nucleolar protein results in alteration of one of these functions, E6 nucleolar localization and/or alteration of nucleolar organization. In a preferred embodiment, the nucleolar protein is a nucleophosmin, e.g. having a sequence given by GenBank accession number X16934.

In yet another embodiment, the cellular E6-binding protein is an apoferritin, preferably an apoferritin having the sequence provided by GenBank accession number X00318. The binding of E6 to the apoferritin protein could, for example, alter the regulation of oxidative events in the PV-infected cells, e.g. altering the ability of the cell to respond to oxidate damage. The binding of apoferritin could, either directly or through changes in the oxidative state of the cell, alter the expression of other cellular proteins important for neoplastic transformation, e.g. for the cell to enter crisis, such as the heat shock proteins. Moreover, transcriptional activation and repression of viral genes by E2 expression and DNA replication and has been suggested to be modulated by changes in the intracellular redox environment. Agents which inhibit the interaction could therefore be useful in preventing papillomavirus infection and/or transformation.

In a further embodiment, the cellular E6-binding protein is a nuclear ribonucleoprotein, preferably a C protein of the nuclear ribonucleoprotein particle C, such as provided by ATCC accession number M16342, or alternatively, a ribonucleoprotein E such as represented by the GenBank accession number X12466. The association of E6 with certain proteins involved in RNA processing reactions suggests a role for E6 which includes the direct regulation of expression of cellular and/or viral genes by post-transcriptional control of RNA splicing. Another role of such interactions with E6 could be to provide a nuclear localization signal for the protein by causing sequestration of E6 in the nucleus. Such an interaction is also a potential therapeutic target for inhibitors of papillomavirus infection and/or transformation.

In a still further embodiment, the E6-binding protein is a complement decay accelerating factor, such as represented in GenBank accession number M15799.

In yet another embodiment, the E6-binding protein is a proteasome subunit, such as the proteasome subunit HC8 represented by GenBank accession number D00762. The binding of E6 to proteosome subunits could provide a mechanism for recruiting protease complexes to other complexes involving E6 in order to facilitate/enhance degradation of proteins bound to E6, such as p53.

In addition to the discovery of the interaction of E6 with cellular proteins which have been previously cloned, a number of novel proteins are identified herein as possessing E6-binding capabilities. It is probable that the binding of E6 to these proteins causes, for example, alteration in the cellular function of these proteins and/or alteration in the localization of one or both of the E6 protein and E6-BP. Thus, while all aspects of the normal cellular role of certain of these proteins has not been fully elucidated, the fact that these proteins bind to the viral E6 protein, and that E6 is critical to the pathology of papillomavirus infection, shows that the interaction of each of these proteins with E6 provides potential therapeutic targets for developing agents which are useful in treating, for example, HPV infection.

For instance, in one embodiment, the E6-binding protein includes a protein sequence represented by SEQ ID No: 8 (clone SD-7), e.g. a polypeptide which binds a papillomavirus E6 protein; e.g. the E6-BP comprises one or more calcium binding motifs, e.g. EF hand motifs; e.g. the E6-BP comprises an ER/trans-golgi localization signal, e.g. a carboxy-terminal His-Asp-Glu-Leu (KDEL) sequence.

In another embodiment, the E6-binding protein is a human homolog of a molecular chaperone protein, such as the human chaperonin 10 protein represented by SEQ ID No: 12 (clone SD-22).

In yet further preferred embodiments: the E6-binding protein comprises a polypeptide represented by one of SEQ ID Nos: 9, 10, 11, 13 or 14 (clones SD-8, SD-12, SD-16, SD28, and SD-32 respectively), e.g. a polypeptide which binds a papillomavirus E6 protein.

Another aspect of the invention pertains to an isolated nucleic acid comprising the nucleotide sequence encoding one of the subject E6-binding proteins, and/or equivalents of such nucleic acids. The term nucleic acid as used herein is intended to include fragments and equivalents. The term equivalent is understood to include nucleotide sequences encoding functionally equivalent E6-binding proteins or functionally equivalent peptides which, for example, retain the ability to bind to E6, and which may additionally retain other activities of an E6-BP such as described herein. Equivalent nucleotide sequences will include sequences that differ by one or more nucleotide substitutions, additions or deletions, such as allelic variants; and will, therefore, include sequences that differ from the nucleotide sequence E6-binding proteins shown in any of SEQ ID Nos: 1–7 due to the degeneracy of the genetic code. Equivalents will also include nucleotide sequences that hybridize under stringent conditions (i.e., equivalent to about 20°–27° C. below the melting temperature ($T_m$) of the DNA duplex formed in about 1M salt) to the nucleotide sequence of the presently claimed E6-binding proteins represented in SEQ ID Nos: 1–7, or to the nucleotide sequence of an E6-binding protein from the pRS306-E6BP library (ATCC accession No: 75827). In one embodiment, equivalents will further include nucleic acid sequences derived from and evolutionarily related to, a nucleotide sequences shown in any of SEQ ID Nos: 1–7.

Moreover, it will be generally appreciated that, under certain circumstances, it may be advantageous to provide, homologs of the subject E6-binding proteins which function in a limited capacity as one of either an E6-BP agonists or an E6-BP antagonist, in order to promote or inhibit only a subset of the biological activities of the naturally-occurring form of the protein. Thus, specific biological effects can be elicited by treatment with a homolog of limited function, and with fewer side effects relative to treatment with agonists or antagonists which are directed to all of an E6-binding proteins biological activities.

Such homologs of the subject E6-binding proteins can be generated by mutagenesis, such as by discrete point mutation(s) or by truncation. For instance, mutation can give rise to homologs which retain substantially the same, or merely a subset, of the biological activity of the E6-BP from which it was derived. Alternatively, antagonistic forms of the protein can be generated which are able to inhibit the function of the naturally occurring form of the protein, such as by competitively binding to E6.

A protein has E6-BP biological activity if it has one or more of the following properties: the ability to modulate proliferation/cell growth of a eukaryotic cell, e.g. a mammalian cell, e.g. a human cell; the ability to modulate the efficacy of papillomavirus infection, e.g. human papillomaviruses, e.g. infection by HPV-16, HPV-18, HPV-31 or HPV-33; the ability to affect the efficacy of cell transformation, e.g. PV-mediated transformation, e.g. PV-mediated transformation, e.g. high risk HPV-mediated transformation; the ability to affect the efficacy of cellular immortalization, e.g. PV-mediated transformation, e.g. HPV-mediated transformation, e.g. high risk HPV-mediated immortalization; or the ability to bind a PV E6 protein, e.g. an HPV E6 protein, e.g. a high risk HPV E6 protein. A protein also has biological activity if it is a specific agonist or antagonist of one of the above recited properties.

As used herein, the term "gene" or "recombinant gene" refers to a nucleic acid comprising an open reading frame encoding an E6-binding protein of the present invention, including both exon and (optionally) intron sequences. A "recombinant gene" refers to nucleic acid encoding an E6-binding protein and comprising E6-BP encoding exon sequences, though it may optionally include intron sequences which are either derived from a chromosomal E6-BP gene or from an unrelated chromosomal gene. Exemplary recombinant genes encoding the subject E6-binding proteins are represented by any one of SEQ ID Nos: 1–7. Moreover, recombinant genes encoding each of the subject E6-binding proteins can be isolated from ATCC deposit No: 75827, as described below. The term "intron" refers to a DNA sequence present in a given E6-BP gene which is not translated into protein and is generally found between exons.

As used herein, the term "transfection" means the introduction of a nucleic acid, e.g., an expression vector, into a recipient cell by nucleic acid-mediated gene transfer. "Transformation", as used herein, refers to a process in which a cell's genotype is changed as a result of the cellular uptake of exogenous DNA or RNA, and, for example, the transformed cell expresses a recombinant form of the E6-binding protein of the present invention or where antisense expression occurs from the transferred gene, the expression of a naturally-occurring form of the E6-binding protein is disrupted.

As used herein, the term "vector" refers to a nucleic acid molecule capable of transporting another nucleic acid to which it has been linked. One type of preferred vector is an episome, i.e., a nucleic acid capable of extra-chromosomal replication. Preferred vectors are those capable of autonomous replication and/or expression of nucleic acids to which they are linked. Vectors capable of directing the expression of genes to which they are operatively linked are referred to herein as "expression vectors". In general, expression vectors of utility in recombinant DNA techniques are often in the form of "plasmids" which refer to circular double stranded DNA loops which, in their vector form are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto.

"Transcriptional regulatory sequence" is a generic term used throughout the specification to refer to DNA sequences, such as initiation signals, enhancers, and promoters, which induce or control transcription of protein coding sequences with which they are operably linked. In preferred embodiments, transcription of a recombinant E6-BP gene is under the control of a promoter sequence (or other transcriptional regulatory sequence) which controls the expression of the recombinant gene in a cell-type in which expression is intended. It will also be understood that the recombinant gene can be under the control of transcriptional regulatory sequences which are the same or which are different from those sequences which control transcription of the naturally-occurring form of the E6-binding protein.

As used herein, the term "tissue-specific promoter" means a DNA sequence that serves as a promoter, i.e., regulates expression of a selected DNA sequence operably linked to the promoter, and which effects expression of the selected DNA sequence in specific cells of a tissue, such as cells of a epithelial lineage, e.g. cervical squamous cells. In the illustrative embodiment of epithelial-specific promoters, gene constructs can be used as a part of gene therapy to deliver, for example, an E6-BP antagonist in order to modulate levels of E6/E6-BP complexes comprising one of the subject E6-binding proteins in papillomavirus-mediated disorders, e.g. pappilomas, or to direct expression of an antisense construct of one of the subject E6-binding proteins in only epithelial tissue. The term also covers so-called "leaky" promoters, which regulate expression of a selected DNA primarily in one tissue, but cause expression in other tissues as well.

As used herein, a "transgenic animal" is any animal, preferably a non-human mammal, e.g. a rat, a mouse or pig, in which one or more of the cells of the animal includes a transgene. The transgene is introduced into the cell, directly or indirectly by introduction into a precursor of the cell, by way of deliberate genetic manipulation, such as by microinjection or by infection with a recombinant virus. The term genetic manipulation does not include classical cross-breeding, or in vitro fertilization, but rather is directed to the introduction of a recombinant DNA molecule. This molecule may be integrated within a chromosome, or it may be extrachromosomally replicating DNA. In the transgenic animals described herein, the transgene causes cells to express a recombinant form of one or more of the subject E6-binding proteins, or alternatively, to disrupt expression of one or more of the naturally-occurring forms of the E6-BP genes.

As used herein, the term "transgene" means a nucleic acid sequence (encoding, e.g., one or more hematopoietic peptides), which is partly or entirely heterologous, i.e., foreign, to the transgenic animal or cell into which it is introduced, or, is homologous to an endogenous gene of the transgenic animal or cell into which it is introduced, but which is designed to be inserted, or is inserted, into the animal's genome in such a way as to alter the genome of the cell into which it is inserted (e.g., it is inserted at a location which differs from that of the natural gene or its insertion results in a knockout). A transgene can include one or more transcriptional regulatory sequences and any other nucleic acid, such as introns, that may be necessary for optimal expression of a selected nucleic acid.

As is well known, genes for a particular polypeptide may exist in single or multiple copies within the genome of an individual. Such duplicate genes may be identical or may have certain modifications, including nucleotide substitutions, additions or deletions, which all still code for polypeptides having substantially the same activity. The term "DNA sequence encoding an E6-binding protein" may thus refer to one or more genes within a particular individual. Moreover, certain differences in nucleotide sequences may exist between individual organisms, which are called alleles. Such allelic differences may or may not result in differences in amino acid sequence of the encoded polypeptide yet still encode a protein with the same biological activity.

"Cells," "host cells" or "recombinant host cells" are terms used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A "chimeric protein" or "fusion protein" is a fusion of a first amino acid sequence encoding one of the subject E6-binding proteins with a second amino acid sequence defining a domain foreign to and not substantially homologous with any domain of the subject E6-BP. A chimeric protein may present a foreign domain which is found (albeit in a different protein) in an organism which also expresses the first protein, or it may be an "interspecies", "intergeneric", etc. fusion of protein structures expressed by different kinds of organisms.

The term "evolutionarily related to", with respect to nucleic acid sequences encoding E6-binding protein, refers to nucleic acid sequences which have arisen naturally in an organism, including naturally occurring mutants. The term also refers to nucleic acid sequences which, while derived from a naturally occurring E6-BP, have been altered by mutagenesis, as for example, combinatorial mutagenesis described below, yet still encode polypeptides which have at least one activity of an E6-binding protein.

In one embodiment, the nucleic acid is a cDNA encoding a peptide having at least one activity of a subject E6-binding protein. Preferably, the nucleic acid is a cDNA molecule comprising at least a portion of the nucleotide sequence represented in one of SEQ ID Nos: 1–7. A preferred portion of these cDNA molecules includes the coding region of the gene.

Preferred nucleic acids encode an E6-binding protein comprising an amino acid sequence at least 60% homologous, more preferably 70% homologous and most preferably 80%, 90%, or 95% homologous with an amino acid sequence shown in one of SEQ ID Nos: 8–14. Nucleic acids which encode polypeptides having an activity of a subject E6-binding protein and having at least about 90%, more preferably at least about 95%, and most preferably at least about 98–99% homology with a sequence shown in one of SEQ ID Nos: 8–14 are also within the scope of the invention. Homology refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. The degree of homology between sequences is a function of the number of matching or homologous positions shared by the sequences.

Certain of the nucleotide sequences shown in the appended sequence listing encode portions of the subject E6-binding proteins. Therefore, in a further embodiment of the invention, the recombinant E6-BP genes can include, in addition to nucleotides encoding the amino acid sequences shown in SEQ. ID. Nos: 1–7, additional nucleotide sequences which encode amino acids at the C-terminus and N-terminus of each protein. For instance, a recombinant E6-BP gene can include nucleotide sequences of a PCR fragment generated by amplifying one of the coding sequences for one of the E6-BP clones of ATCC deposit No: 75827 using sets of primers derived from Table 1 below.

Another aspect of the invention provides a nucleic acid which hybridizes under high or low stringency conditions to a nucleic acid which encodes a peptide having all or a portion of an amino acid sequence shown in SEQ ID No: 8, SEQ ID No: 9, SEQ ID No: 10, SEQ ID No: 11, SEQ ID No: 12, SEQ ID No: 13 or SEQ ID No: 14. Appropriate stringency conditions which promote DNA hybridization, for example, 6.0×sodium chloride/sodium citrate (SSC) at about 45° C., followed by a wash of 2.0×SSC at 50° C., are known to those skilled in the art or can be found in *Current Protocols in Molecular Biology*, John Wiley & Sons, New York (1989), 6.3.1–6.3.6. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C.

Nucleic acids, having a sequence that differs from the nucleotide sequence shown any of SEQ ID Nos: 1–7 due to degeneracy in the genetic code are also within the scope of the invention. Such nucleic acids encode functionally equivalent peptides (i.e., a peptide having a biological activity of an E6-binding protein) but differ in sequence from the sequence shown in said sequence listings due to degeneracy in the genetic code. For example, a number of amino acids are designated by more than one triplet. Codons that specify the same amino acid, or synonyms (for example, CAU and CAC each encode histidine) may result in "silent" mutations which do not affect the amino acid sequence of the E6-binding protein. However, it is expected that DNA sequence polymorphisms that do lead to changes in the amino acid sequences of the subject E6-binding proteins will exist among vertebrates. One skilled in the art will appreciate that these variations in one or more nucleotides (up to about 3–5% of the nucleotides) of the nucleic acids encoding polypeptides having an activity of an E6-binding protein may exist among individuals of a given species due to natural allelic variation. Any and all such nucleotide variations and resulting amino acid polymorphisms are within the scope of this invention.

Fragments of the nucleic acids encoding the active portion of the presently claimed E6-binding proteins are also within the scope of the invention. As used herein, a fragment of the nucleic acid encoding the active portion of an E6-binding protein refers to a nucleic acid having fewer nucleotides than the nucleotide sequence encoding the entire amino acid sequence of an E6-binding protein but which nevertheless encodes a peptide having an E6-BP biological activity, e.g.) an agonist activity of an E6-binding protein. Nucleic acid fragments within the scope of the present invention include those capable of hybridizing under high or low stringency conditions with nucleic acids from other species for use in screening protocols to detect E6-BP homologs, as well as those capable of hybridizing with nucleic acids from human specimens for use in detecting the presence of a nucleic acid encoding one of the subject E6-BPs, including alternate isoforms, e.g. mRNA splicing variants. Nucleic acids within the scope of the invention may also contain linker sequences, modified restriction endonuclease sites and other sequences useful for molecular cloning, expression or purification of recombinant forms of the subject E6-binding proteins.

As indicated by the examples set out below, a nucleic acid encoding a peptide having an activity of an E6-binding protein may be obtained from mRNA present in any of a number of eukaryotic cells. It should also be possible to obtain nucleic acids encoding E6-binding proteins of the present invention from genomic DNA obtained from both adults and embryos. For example, a gene encoding an E6-binding protein can be cloned from either a cDNA or a genomic library in accordance with protocols herein described, as well as those generally known to persons skilled in the art. A cDNA encoding one of the subject E6-binding proteins can be obtained by isolating total mRNA from a cell, e.g. a mammalian cell, e.g. a human cell, including tumor cells. Double stranded cDNAs can then be prepared from the total mRNA, and subsequently inserted into a suitable plasmid or bacteriophage vector using any one of a number of known techniques. The gene encoding the E6-binding protein can also be cloned using established polymerase chain reaction techniques in accordance with the nucleotide sequence information provided by the invention.

The nucleic acid of the invention can be DNA or RNA. A preferred nucleic acid is a cDNA represented by the sequence shown in SEQ ID No: 1; e.g. provided that the nucleic acid hybridizes to a nucleic acid probe comprising a subsequence preferably encoding at least four consecutive amino acid residues between residues 1 and 133 of SEQ ID No: 8, more preferably at least ten consecutive amino acid residues, more preferably at least twenty consecutive amino acid residues. Another nucleic acid is a cDNA represented by the sequence shown in SEQ ID No: 2. Other preferred nucleic acids include cDNA molecules represented by the sequences shown in one of SEQ ID Nos: 3–7. A preferred nucleic acid is a cDNA derived from the pRS306-E6BP library (ATCC deposit No: 75827).

This invention also provides expression vectors containing a nucleic acid encoding a peptide having an activity of an E6-binding protein, operably linked to at least one transcriptional regulatory sequence. Operably linked is intended to mean that the nucleotide sequence is linked to a regulatory sequence in a manner which allows expression of the nucleotide sequence. Regulatory sequences are art-recognized and are selected to direct expression of the peptide having an activity of an E6-binding protein. Accordingly, the term transcriptional regulatory sequence includes promoters, enhancers and other expression control elements. Such regulatory sequences are described in Goeddel; *Gene Expression Technology: Methods in Enzymology* 185, Academic Press, San Diego, Calif. (1990). It should be understood that the design of the expression vector may depend on such factors as the choice of the host cell to be transformed and/or the type of protein desired to be expressed. In one embodiment, the expression vector includes a recombinant gene encoding a peptide having an activity of a subject E6-binding protein, or alternatively, encoding a peptide which is an antagonistic form of the subject E6-binding protein. Such expression vectors can be used to transfect cells and thereby produce proteins or peptides, including fusion proteins or peptides, encoded by nucleic acids as described herein.

Moreover, such vectors can be used as a part of a gene therapy protocol to reconstitute the function of, or alternatively, abrogate the function of one of the subject E6-binding proteins in a cell in which that E6-BP is misexpressed. Illustrative examples of therapeutic vehicles useful for delivery of an E6-BP construct to a target cell are disclosed in, for example, PCT publication WO 93/04701, PCT publication WO 92/22635, PCT publication WO 92/20316, PCT publication WO 92/19749, and PCT publication WO 92/06180.

Another aspect of the present invention concerns recombinant forms of the subject E6-binding proteins which are encoded by genes derived from eukaryotic organisms, e.g. mammals, e.g. humans, and which have at least one biological activity of an E6-binding protein, e.g., which is an antagonist of at least one activity of an E6-BP of the present invention, including naturally occurring dysfunctional mutants. The term "recombinant protein" refers to a protein of the present invention which is produced by recombinant DNA techniques, wherein generally DNA encoding the subject E6-binding protein is inserted into a suitable expression vector which is in turn used to transform a host cell to produce the heterologous protein. Moreover, the phrase "derived from", with respect to a recombinant gene encoding the recombinant E6-BP, is meant to include within the meaning of "recombinant protein" those proteins having an amino acid sequence of a native E6-BP of the present invention, or an amino acid sequence similar thereto which is generated by mutations including substitutions and deletions (including truncation) of a naturally occurring E6-binding protein of a organism. Recombinant proteins preferred by the present invention, in addition to native E6-binding proteins, are at least 60% homologous, more preferably 70% homologous and most preferably 80% homologous with an amino acid sequence shown in one of SEQ ID Nos: 8–14. Polypeptides having an activity of the subject E6-binding proteins (i.e. either agonistic or antagonistic) and having at least about 90%, more preferably at least about 95%, and most preferably at least about 98–99% homology with a sequence of either in SEQ ID No: 8–14 are also within the scope of the invention.

The present invention further pertains to recombinant forms of the subject E6-binding proteins which are encoded by genes derived from a organism and which have amino acid sequences evolutionarily related to an E6-binding protein of any of SEQ ID Nos: 8–14. Such recombinant E6-binding proteins preferably are capable of functioning in one of either role of an agonist or antagonist of at least one biological activity of the present E6-BPs. The term "evolutionarily related to", with respect to amino acid sequences of the present recombinant E6-binding proteins, refers to E6-binding proteins having amino acid sequences which have arisen naturally, as well as mutational variants of E6-binding proteins which are derived, for example, by combinatorial mutagenesis. Such evolutionarily derived E6-binding protein preferred by the present invention are at least 60% homologous, more preferably 70% homologous and most preferably 80% homologous with an amino acid sequence shown in either SEQ ID No: 8, SEQ ID No: 9, SEQ ID No: 10, SEQ ID No: 11, SEQ ID No: 12, SEQ ID No: 13 or SEQ ID No: 14. Polypeptides having at least about 90%, more preferably at least about 95%, and most preferably at least about 98–99% homology with a sequence shown in any of SEQ ID Nos: 8–14 are also within the scope of the invention.

The present invention further pertains to methods of producing the subject E6-binding proteins. For example, a host cell transfected with a nucleic acid vector directing expression of a nucleotide sequence encoding the subject E6-binding protein can be cultured under appropriate conditions to allow expression of the peptide to occur. The peptide may be secreted and isolated from a mixture of cells and medium containing the recombinant E6-BP. Alternatively, the peptide may be retained cytoplasmically and the cells harvested, lysed and the protein isolated. A cell culture includes host cells, media and other byproducts. Suitable media for cell culture are well known in the art. The recombinant E6-BP peptide can be isolated from cell culture medium, host cells, or both using techniques known in the art for purifying proteins including ion-exchange chromatography, gel filtration chromatography, ultrafiltration, electrophoresis, and immunoaffinity purification with antibodies specific for such peptide. In a preferred embodiment, the recombinant E6-binding protein is a fusion protein containing a domain which facilitates its purification, such as an E6-BP-GST fusion protein.

This invention also pertains to a host cell transfected to express a recombinant form of at least one of the subject E6-binding proteins. The host cell may be any prokaryotic or eukaryotic cell. Thus, a nucleotide sequence derived from the cloning of the E6-binding proteins of the present invention, encoding all or a selected portion of a protein, can be used to produce a recombinant form of an E6-BP via microbial or eukaryotic cellular processes. Ligating the polynucleotide sequence into a gene construct, such as an expression vector, and transforming or transfecting into hosts, either eukaryotic (yeast, avian, insect or mammalian) or prokaryotic (bacterial cells), are standard procedures used in producing other well-known proteins, e.g. insulin, interferons, human growth hormone, IL-1, IL-2, and the like. Similar procedures, or modifications thereof, can be employed to prepare recombinant E6-binding proteins, or portions thereof, by microbial means or tissue-culture technology in accord with the subject invention.

The recombinant E6-binding gene can be produced by ligating nucleic acid encoding a subject E6-binding protein, or a portion thereof, into a vector suitable for expression in either prokaryotic cells, eukaryotic cells, or both. Expression vectors for production of recombinant forms of the subject E6-binding proteins include plasmids and other vectors. For instance, suitable vectors for the expression of an E6-BP include plasmids of the types: pBR322-derived plasmids, pEMBL-derived plasmids, pEX-derived plasmids, pBTac-derived plasmids and pUC-derived plasmids for expression in prokaryotic cells, such as E. coli.

A number of vectors exist for the expression of recombinant proteins in yeast. For instance, YEP24, YIP5, YEP51, YEP52, pYES2, and YRP17 are cloning and expression vehicles useful in the introduction of genetic constructs into S. cerevisiae (see, for example, Broach et al. (1983) in Experimental Manipulation of Gene Expression, ed. M. Inouye Academic Press, p. 83, incorporated by reference herein). These vectors can replicate in E. coli due the presence of the pBR322 ori, and in S. cerevisiae due to the replication determinant of the yeast 2 micron plasmid. In addition, drug resistance markers such as ampicillin can be used. In an illustrative embodiment, an E6-binding protein is produced recombinantly utilizing an expression vector generated by sub-cloning a gene encoding the protein from pRS306-E6BP library (ATCC accession No: 75827) using, for example, primers based on SEQ ID No: 1–7 and/or primers based on the flanking plasmid sequence (e.g. the primers represented by SEQ ID Nos: 15–17).

The preferred mammalian expression vectors contain both prokaryotic sequences to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papilloma virus (BPV-1), or Epstein-Barr virus (pHEBo, pREP-derived and p205) can be used for transient expression of proteins in eukaryotic cells. The various methods employed in the preparation of the plasmids and transformation of host organisms are well known in the art. For other suitable expression systems for both prokaryotic and eukaryotic cells, as well as general recombinant procedures, see Molecular Cloning A Laboratory Manual, 2nd Ed., ed. by Sambrook, Fritsch and Maniatis (Cold Spring Harbor Laboratory Press: 1989) Chapters 16 and 17. In some instances, it may be desirable to express the recombinant E6-BP by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the β-gal containing pBlueBac III).

When expression of a portion of one of the subject E6-binding protein is desired, i.e. a trunction mutant, it may be necessary to add a start codon (ATG) to the oligonucleotide fragment containing the desired sequence to be expressed. It is well known in the art that a methionine at the N-terminal position can be enzymatically cleaved by the use of the enzyme methionine aminopeptidase (MAP). MAP has been cloned from *E. coli* (Ben-Bassat et al. (1987) *J. Bacteriol.* 169:751–757) and *Salmonella typhimurium* and its in vitro activity has been demonstrated on recombinant proteins (Miller et al. (1987) *PANAS* 84:2718–1722). Therefore, removal of an N-terminal methionine, if desired, can be achieved either in vivo by expressing E6-BP-derived polypeptides in a host which produces MAP (e.g., *E. coli* or CM89 or *S. cerevisiae*), or in vitro by use of purified MAP (e.g., procedure of Miller et al., supra).

Alternatively, the coding sequences for the polypeptide can be incorporated as a part of a fusion gene including a nucleotide sequence encoding a different polypeptide. This type of expression system can be useful under conditions where it is desirable to produce an immunogenic fragment of an E6-binding protein For example, the VP6 capsid protein of rotavirus can be used as an immunologic carrier protein for portions of the E6-BP polypeptide, either in the monomeric form or in the form of a viral particle. The nucleic acid sequences corresponding to the portion of a subject E6-binding protein to which antibodies are to be raised can be incorporated into a fusion gene construct which includes coding sequences for a late vaccinia virus structural protein to produce a set of recombinant viruses expressing fusion proteins comprising a portion of the protein E6-BP as part of the virion. It has been demonstrated with the use of immunogenic fusion proteins utilizing the Hepatitis B surface antigen fusion proteins that recombinant Hepatitis B virions can be utilized in this role as well. Similarly, chimeric constructs coding for fusion proteins containing a portion of an E6-binding protein and the poliovirus capsid protein can be created to enhance immunogenicity of the set of polypeptide antigens (see, for example, EP Publication No: 0259149; and Evans et al. (1989) *Nature* 339:385; Huang et al. (1988) *J. Virol.* 62:3855; and Schlienger et al. (1992) *J. Virol.* 66:2).

The Multiple Antigen Peptide system for peptide-based immunization can also be utilized to generate an immunogen, wherein a desired portion of a subject E6-binding protein is obtained directly from organochemical synthesis of the peptide onto an oligomeric branching lysine core (see, for example, Posnett et al. (1988) *JBC* 263:1719 and Nardelli et al. (1992) *J. Immunol.* 148:914). Antigenic determinants of the subject E6-binding proteins can also be expressed and presented by bacterial cells.

In addition to utilizing fusion proteins to enhance immunogenicity, it is widely appreciated that fusion proteins can also facilitate the expression of proteins, such as any one of the E6-binding protein of the present invention. For example, as described below, an E6-binding protein of the present invention can be generated as a glutathione-S-transferase (GST-fusion protein). Such GST fusion proteins can enable easy purification of the E6-binding protein, such as by the use of glutathione-derivatized matrices (see, for example, *Current Protocols in Molecular Biology*, eds. Ausubel et al. (New York: John Wiley & Sons, 1991)). In another embodiment, a fusion gene coding for a purification leader sequence, such as a poly(His)/enterokinase cleavage site sequence at the N-terminus of the desired portion of the E6-binding protein, can allow purification of the poly(His) -expressed E6-BP-fusion protein by affinity chromatography using a $Ni^{2+}$ metal resin. The purification leader sequence can then be subsequently removed by treatment with enterokinase (e.g., see Hochuli et al. (1987) *J. Chromatography* 411:177; and Janknecht et al. *PNAS* 88:8972).

Techniques for making fusion genes are known to those skilled in the art. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed to generate a chimeric gene sequence (see, for example, *Current Protocols in Molecular Biology*, eds. Ausubel et al. John Wiley & Sons: 1992).

Another aspect of the invention pertains to isolated peptides having an activity of one of the subject E6-binding protein, or which are antagonists of at least one of the biological activities of the subject E6-BPs. In preferred embodiments, a biological activity of an E6-binding protein includes: an ability to modulate proliferation/cell growth of a eukaryotic cell, e.g. a mammalian cell, e.g. a human cell; an ability to affect the efficacy of papillomavirus infection, e.g. infection by HPV-16, HPV-18, HPV-31 or HPV-33; an ability to affect the efficacy of cell transformation, e.g. PV-mediated transformation, e.g. PV-mediated transformation, e.g. high risk HPV-mediated transformation; an ability to affect the efficacy of cellular immortalization, e.g. PV-mediated transformation, e.g. HPV-mediated transformation, e.g. high risk HPV-mediated immortalization; an ability to bind a PV E6 protein, e.g. an HPV E6 protein, e.g. a high risk HPV E6 protein. E6-binding proteins of the present invention, particularly those with antagonistic activity, can have the ability to suppress tumor growth, e.g. in a tumor cell in which endogenous E6-BP is misexpressed. Other biological activities of the subject E6-binding proteins are described herein or will be reasonably apparent to those skilled in the art. A polypeptide having at least one biological activity of the subject E6-binding proteins may differ in amino acid sequence from the sequence shown in either SEQ ID Nos: 8–14, but such differences result in a modified protein which functions in the same or similar manner as the native E6-binding protein or which has the same or similar characteristics of the native E6-binding protein. Various modifications of a E6-binding protein of the present invention to produce these and other functionally equivalent peptides are described in detail herein. The term peptide, as used herein, refers to peptides, proteins, and polypeptides.

The present invention also makes available isolated E6-binding proteins which are isolated from, or otherwise substantially free of other cellular or viral proteins, especially papillomavirus proteins, normally associated with the E6-binding protein. The term "substantially free of other cellular or viral proteins" (also referred to herein as "contaminating proteins") or "substantially pure or purified preparations" are defined as encompassing E6-BP preparations having less than 20% (by dry weight) contaminating protein, and preferably having less than 5% contaminating protein. Functional forms of the subject E6-binding proteins can be prepared, for the first time, as purified preparations by using a cloned gene as described herein. By "purified", it is meant, when referring to a peptide or DNA or RNA sequence, that the indicated molecule is present in the substantial absence of other biological macromolecules, such as other proteins (particularly viral proteins such as E6, as well as other contaminating proteins). The term "purified" as used herein preferably means at least 80% by dry weight, more preferably in the range of 95–99% by weight, and most preferably at least 99.8% by weight, of biological macromolecules of the same type present (but water, buffers, and other small molecules, especially molecules having a molecular weight of less than 5000, can be present). The term "pure" as used herein preferably has the same numerical limits as "purified" immediately above. "Isolated" and "purified" do not encompass either natural materials in their native state or natural materials that have been separated into components (e.g., in an acrylamide gel) but not obtained either as pure (e.g. lacking contaminating proteins, or chromatography reagents such as denaturing agents and polymers, e.g. acrylamide or agarose) substances or solutions.

The term "isolated" as also used herein with respect to nucleic acids, such as DNA or RNA, refers to molecules separated from other DNAs, or RNAs, respectively, that are present in the natural source of the macromolecule. For example, an isolated nucleic acid encoding one of the subject E6-binding proteins preferably includes no more than 10 kilobases (kb) of nucleic acid sequence which naturally immediately flanks that particular E6-BP gene in genomic DNA, more preferably no more than 5 kb of such naturally occurring flanking sequences, and most preferably less than 1.5 kb of such naturally occurring flanking sequence. The term isolated as used herein also refers to a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state.

Furthermore, isolated peptidyl portions of the subject E6-binding proteins can also be obtained by screening peptides recombinantly produced from the corresponding fragment of the nucleic acid encoding such peptides. In addition, fragments can be chemically synthesized using techniques known in the art such as conventional Merrifield solid phase f-Moc or t-Boc chemistry. For example, an E6-binding protein of the present invention may be arbitrarily divided into fragments of desired length with no overlap of the fragments, or preferably divided into overlapping fragments of a desired length. The fragments can be produced (recombinantly or by chemical synthesis) and tested to identify those peptidyl fragments which can function as either agonists or antagonists of an E6-binding protein activity, such as by microinjection assays.

It is possible to modify the structure of the subject E6-binding proteins for such purposes as enhancing therapeutic or prophylactic efficacy, or stability (e.g., ex vivo shelf life and resistance to proteolytic degradation in vivo). Such modified peptides, when designed to retain at least one activity of the naturally-occurring form of the protein, are considered functional equivalents of the E6-binding protein described in more detail herein. Such modified peptide can be produced, for instance, by amino acid substitution, deletion, or addition.

Moreover, it is reasonable to expect that an isolated replacement of a leucine with an isoleucine or valine, an aspartate with a glutamate, a threonine with a serine, or a similar replacement of an amino acid with a structurally related amino acid (i.e. conservative mutations) will not have a major effect on the biological activity of the resulting molecule. Conservative replacements are those that take place within a family of amino acids that are related in their side chains. Genetically encoded amino acids are can be divided into four families: (1) acidic=aspartate, glutamate; (2) basic=lysine, arginine, histidine; (3) nonpolar=alanine, valine, leucine, isoleucine, proline, phenylalanine, methionine, tryptophan; and (4) uncharged polar=glycine, asparagine, glutamine, cysteine, serine, threonine, tyrosine. Phenylalanine, tryptophan, and tyrosine are sometimes classified jointly as aromatic amino acids. In similar fashion, the amino acid repertoire can be grouped as (1) acidic=aspartate, glutamate; (2) basic=lysine, arginine histidine, (3) aliphatic= glycine, alanine, valine, leucine, isoleucine, serine, threonine, with serine and threonine optionally be grouped separately as aliphatic-hydroxyl; (4) aromatic= phenylalanine, tyrosine, tryptophan; (5) amide=asparagine, glutamine; and (6) sulfur-containing=cysteine and methionine. (see, for example, *Biochemistry*, 2nd ed., Ed. by L. Stryer, W. H. Freeman and Co.: 1981). Whether a change in the amino acid sequence of a peptide results in a functional E6-BP homolog can be readily determined by assessing the ability of the variant peptide to produce a response in cells in a fashion similar to the wild-type E6-BP. Peptides in which more than one replacement has taken place can readily be tested in the same manner.

This invention further contemplates a method of generating sets of combinatorial mutants of the presently disclosed novel E6-binding proteins, as well as truncation mutants, and is especially useful for identifying potential variant sequences which are functional in binding to a PV E6 protein, especially an E6 protein of a high risk HPV. One purpose for screening such combinatorial libraries is, for example, to isolate novel E6-BP homologs which function as one of either an agonist or antagonist of the biological activities of the wild-type ("authentic") protein, or alternatively, possess novel activities all together. To illustrate, E6-BP homologs can be engineered by the present method to provide proteins which bind E6 yet which act antagonistically to the role of the native E6-BP in papillomavirus infection, transformation and/or immortalization. Such proteins, when expressed from recombinant DNA constructs, can be used in gene therapy protocols.

Likewise, mutagenesis can give rise to E6-BP homologs which have intracellular half-lives dramatically different than the corresponding wild-type protein. For example, the altered protein can be rendered either more stable or less stable to proteolytic degradation or other cellular process which result in destruction of, or otherwise inactivation of, an E6-binding protein. Such E6-BP homologs and the genes which encode them, can be utilized to alter the envelope of expression for the particular recombinant E6 binding proteins by modulating the half-life of the recombinant protein. For instance, a short half-life can give rise to more transient biological effects associated with a particular recombinant E6-BP and, when part of an inducible expression system, can allow tighter control of recombinant E6-BP levels within the cell. As above, such proteins, and particularly their recombinant nucleic acid constructs, can be used in gene therapy protocols.

In an illustrative embodiment of this method, the amino acid sequences for a population of E6-BP homologs or other related proteins are aligned, preferably to promote the highest homology possible. Such a population of variants can include, for example, E6-BP homologs from one or more species, or E6-BP homologs from the same species but which differ due to mutation. Amino acids which appear at each position of the aligned sequences are selected to create a degenerate set of combinatorial sequences.

In a preferred embodiment, the combinatorial E6-BP library is produced by way of a degenerate library of genes encoding a library of polypeptides which each include at least a portion of potential E6-BP sequences. A mixture of synthetic oligonucleotides can be enzymatically ligated into gene sequences such that the degenerate set of potential E6-BP sequences are expressible as individual polypeptides, or alternatively, as a set of larger fusion proteins (e.g. for phage display) containing the set of E6-BP sequences therein.

There are many ways by which the library of potential E6-BP homologs can be generated from a degenerate oligonucleotide sequence. Chemical synthesis of a degenerate gene sequence can be carried out in an automatic DNA synthesizer, and the synthetic genes then be ligated into an appropriate gene for expression. The purpose of a degenerate set of genes is to provide, in one mixture, all of the sequences encoding the desired set of potential E6-BP sequences. The synthesis of degenerate oligonucleotides is well known in the art (see for example, Narang, SA (1983) *Tetrahedron* 39:3; Itakura et al. (1981) *Recombinant DNA, Proc 3rd Cleveland Sympos. Macromolecules,* ed. A. G. Walton, Amsterdam: Elsevier pp. 273–289; Itakura et al. (1984) *Annu. Rev. Biochem.* 53:323; Itakura et al. (1984) *Science* 198:1056; Ike et al. (1983) *Nucleic Acid Res.* 11:477. Such techniques have been employed in the directed evolution of other proteins (see, for example, Scott et al. (1990) *Science* 249:386–390; Roberts et al. (1992) *PNAS* 89:2429–2433; Devlin et al. (1990) *Science* 249: 404–406; Cwirla et al. (1 990) *PNAS* 87: 6378–6382; as well as U.S. Pat. Nos: 5,223,409, 5,198,346, and 5,096,815).

A wide range of techniques are known in the art for screening gene products of combinatorial libraries made by point mutations, and for screening cDNA libraries for gene products having a certain property. Such techniques will be generally adaptable for rapid screening of the gene libraries generated by the combinatorial mutagenesis of E6-BP homologs. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected. Each of the illustrative assays described below are amenable to high through-put analysis as necessary to screen large numbers of degenerate E6-BP sequences created by combinatorial mutagenesis techniques.

In one screening assay, the candidate E6-BP gene products are displayed on the surface of a cell or viral particle, and the ability of particular cells or viral particles to bind an E6 protein, such HPV-16 E6, via this gene product is detected in a "panning assay". For instance, the gene library can be cloned into the gene for a surface membrane protein of a bacterial cell, and the resulting fusion protein detected by panning (Ladner et al., WO 88/06630; Fuchs et al. (1991) *Bio/Technology* 9:1370–1371; and Goward et al. (1992) *TIBS* 18:136–140). In a similar fashion, fluorescently labeled E6 can be used to score for potentially functional E6-BP homologs. Cells can be visually inspected and separated under a fluorescence microscope, or, where the morphology of the cell permits, separated by a fluorescence-activated cell sorter.

In an alternate embodiment, the gene library is expressed as a fusion protein on the surface of a viral particle. For instance, in the filamentous phage system, foreign peptide sequences can be expressed on the surface of infectious phage, thereby conferring two significant benefits. First, since these phage can be applied to affinity matrices at very high concentrations, a large number of phage can be screened at one time. Second, since each infectious phage displays the combinatorial gene product on its surface, if a particular phage is recovered from an affinity matrix in low yield, the phage can be amplified by another round of infection. The group of almost identical *E. coli* filamentous phages M13, fd., and f1 are most often used in phage display libraries, as either of the phage gIII or gVIII coat proteins can be used to generate fusion proteins without disrupting the ultimate packaging of the viral particle (Ladner et al. PCT publication WO 90/02909; Garrard et al., PCT publication WO 92/09690; Marks et al. (1992) *J. Biol. Chem.* 267:16007–16010; Griffiths et al. (1993) *EMBO J* 12:725–734; Clackson et al. (1991) *Nature* 352:624–628; and Barbas et al. (1992) *PNAS* 89:4457–4461).

In an illustrative embodiment, the recombinant phage antibody system (RPAS, Pharmacia Catalog number 27-9400-01) can be easily modified for use in expressing and screening E6-BP combinatorial libraries. For instance, the pCANTAB 5 phagemid of the RPAS kit contains the gene which encodes the phage gIII coat protein. The E6-BP combinatorial gene library can be cloned into the phagemid adjacent to the gIII signal sequence such that it will be expressed as a gIII fusion protein. After ligation, the phagemid is used to transform competent *E. coli* TG1 cells. Transformed cells are subsequently infected with M13KO7 helper phage to rescue the phagemid and its candidate E6-RP gene insert. The resulting recombinant phage contain phagemid DNA encoding a specific candidate E6-BP, and display one or more copies of the corresponding fusion coat protein. Those phage-displayed candidate E6-BPs which are capable of binding a E6 are selected or enriched by panning with E6. For instance, the phage library can be panned on glutathione immobilized E6-GST fusion proteins, and unbound phage washed away from the cells. The bound phage is then isolated, and if the recombinant phage express at least one copy of the wild type gIII coat protein, they will retain their ability to infect *E. coli*. Thus, successive rounds of reinfection of *E. coli,* and panning will greatly enrich for E6-BP homologs, which can retain an ability to bind E6 which can subsequently be screened for further biological activities in order to differentiate agonists and antagonists.

In light of the present disclosure, other forms of mutagenesis generally applicable will be apparent to those skilled in the art in addition to the aforementioned combinatorial mutagenesis approach. For example, E6-BP homologs (both agonist and antagonist forms) can be generated and screened using, for example, alanine scanning mutagenesis and the like (Ruf et al. (1994) *Biochemistry* 33:1565–1572; Wang et al. (1994) *J. Biol. Chem.* 269:3095–3099; Balint et al. (1993) *Gene* 137:109–118; Grodberg et al. (1993) *Eur. J. Biochem.* 218:597–601; Nagashima et al. (1993) *J. Biol. Chem.* 268:2888–2892; Lowman et al. (1991) *Biochemistry* 30:10832–10838; and Cunningham et al. (1989) *Science* 244:1081–1085), by linker scanning mutagenesis (Gustin et al. (1993) *Virology* 193:653–660; Brown et al. (1992) *Mol. Cell Biol.* 12:2644–2652; McKnight et al. (1982) *Science* 232:316); or by saturation mutagenesis (Meyers et al. (1986) *Science* 232:613).

The invention also provides for reduction of the E6-binding domains of the subject E6-binding proteins to generate mimetics, e.g. peptide or non-peptide agents, which are able to disrupt binding of an E6-BP of the present invention with a papillomavirus E6 protein. Thus, such mutagenic techniques are particularly useful to map the determinants of the E6-BP which participate in protein-protein interactions involved in, for example, binding of the subject E6-binding protein to a PV E6 protein. To illustrate, the critical residues of a subject E6-binding protein which are involved in molecular recognition of E6 can be determined and used to generate E6-BP-derived peptidomimetics which competitively inhibit binding of the E6-BP with E6 (see, for example, "Peptide inhibitors of human papillomavirus protein binding to retinoblastoma gene protein" European patent applications EP-412,762A and EP-B31,080A). By employing, for example, scanning mutagenesis to map the amino acid residues of a particular E6-binding protein involved in binding E6, peptodomimetic compounds (e.g. diazepine or isoquinoline derivatives) can be generated which mimic those residues in binding to E6, and which therefore can inhibit binding of the E6-BP to E6 and thereby interfere with the function of E6 in PV infection. For instance, non-hydrolyzable peptide analogs of such residues can be generated using benzodiazepine (e.g., see Freidinger et al. in *Peptides: Chemistry and Biology*, G. R. Marshall ed., ESCOM Publisher: Leiden, Netherlands, 1988), azepine (e.g., see Huffman et al. in *Peptides: Chemistry and Biology*, G. R. Marshall ed., ESCOM Publisher: Leiden, Netherlands, 1988), substituted gama lactam rings (Garvey et al. in *Peptides: Chemistry and Biology*, G. R. Marshall ed., ESCOM Publisher: Leiden, Netherlands, 1988), keto-methylene pseudopeptides (Ewenson et al. (1986) *J. Med Chem* 29:295; and Ewenson et al. in in *Peptides: Structure and Function* (Proceedings of the 9th American Peptide Symposium) Pierce Chemical Co. Rockland, Ill., 1985), β-turn dipeptide cores (Nagai et al. (1985) *Tetrahedron Lett* 26:047; and Sato et al. (1986) *J. Chem Soc Perkin Trans* 1:1231), and β-aminoalcohols (Gordon et al. (1985) *Biochem Biophys Res Commun* 126:419; and Dann et al. (1986) *Biochem Biophys Res Commun* 134:71).

Another aspect of the invention pertains to an antibody specifically reactive with one of the subject E6-binding proteins. For example, by using immunogens derived from the present activity E6-binding proteins, based on the cDNA sequences, anti-protein/anti-peptide antisera or monoclonal antibodies can be made by standard protocols (See, for example, *Antibodies: A Laboratory Manual* ed. by Harlow and Lane (Cold Spring Harbor Press: 1988)). A mammal such as a mouse, a hamster or rabbit can be immunized with an immunogenic form of the peptide (e.g., E6-binding protein or an antigenic fragment which is capable of eliciting an antibody response). Techniques for conferring immunogenicity on a protein or peptide include conjugation to carriers or other techniques well known in the art. An immunogenic portion of the subject E6-binding proteins can be administered in the presence of adjuvant. The progress of immunization can be monitored by detection of antibody titers in plasma or serum. Standard ELISA or other immunoassays can be used with the immunogen as antigen to assess the levels of antibodies. In a preferred embodiment, the subject antibodies are immunospecific for antigenic determinants of the E6-binding proteins of the present invention, e.g. antigenic determinants of a protein represented by one of SEQ ID Nos: 8–14 or a closely related human or non-human mammalian homolog (e.g. 90 percent homologous, more preferably at least 95 percent homologous). In yet a further preferred embodiment of the present invention, the anti-E6-BP antibodies do not substantially cross react (i.e. react specifically) with a protein which is: e.g. less than 90 percent homologous to one of SEQ ID Nos: 8–14; e.g. less than 95 percent homologous with one of SEQ ID Nos: 8–14; e.g. less than 98–99 percent homologous with one of SEQ ID Nos: 8–14. By "not substantially cross react", it is meant that the antibody has a binding affinity for a non-homologous protein (e.g. E6) which is less than 10 percent, more preferably less than 5 percent, and even more preferably less than 1 percent, of the binding affinity for a protein of SEQ ID Nos: 8–14.

Following immunization, anti-E6-BP antisera can be obtained and, if desired, polyclonal anti-E6-BP antibodies isolated from the serum. To produce monoclonal antibodies, antibody producing cells (lymphocytes) can be harvested from an immunized animal and fused by standard somatic cell fusion procedures with immortalizing cells such as myeloma cells to yield hybridoma cells. Such techniques are well known in the art, an include, for example, the hybridoma technique (originally developed by Kohler and Milstein, (1975) *Nature*, 256: 495–497), the human B cell hybridoma technique (Kozbar et al., (1983) *Immunology Today*, 4: 72), and the EBV-hybridoma technique to produce human monoclonal antibodies (Cole et al., (1985) *Monoclonal Antibodies and Cancer Therapy*, Alan R. Liss, Inc. pp. 77–96). Hybridoma cells can be screened immunochemically for production of antibodies specifically reactive with an E6-binding protein of the present invention and monoclonal antibodies isolated from a culture comprising such hybridoma cells.

The term antibody as used herein is intended to include fragments thereof which are also specifically reactive with one of the subject E6-binding protein. Antibodies can be fragmented using conventional techniques and the fragments screened for utility in the same manner as described above for whole antibodies. For example, F(ab')$_2$ fragments can be generated by treating antibody with pepsin. The resulting F(ab')$_2$ fragment can be treated to reduce disulfide bridges to produce Fab' fragments. The antibody of the present invention is further intended to include bispecific and chimeric molecules having an anti-E6-BP portion.

Both monoclonal and polyclonal antibodies (Ab) directed against E6-BP or E6-BP variants, and antibody fragments such as Fab' and F(ab')$_2$, can be used to block the action of E6-BP and allow the study of the role of a particular E6 binding protein of the present invention in papillomavirus infection, transformation and/or immortalization, as well as the normal cellular function of the E6-binding protein, e.g. by microinjection of anti-E6BP antibodies of the present invention.

Antibodies which specifically bind E6-BP epitopes can also be used in immunohistochemical staining of tissue samples in order to evaluate the abundance and pattern of expression of each of the subject E6-BP. Anti-E6-BP antibodies can be used diagnostically in immuno-precipitation and immuno-blotting to detect and evaluate E6-BP levels in tissue or bodily fluid as part of a clinical testing procedure. For instance, such measurements can be useful in predictive valuations of the onset or progression of HPV infection. Likewise, the ability to monitor E6-BP levels in an individual can allow determination of the efficacy of a given treatment regimen for an individual afflicted with such a disorder. The level of E6-BP can be measured in cells found in bodily fluid, such as in samples of cerebral spinal fluid, or can be measured in tissue, such as produced by biopsy. Diagnostic assays using anti-E6-BP antibodies can include, for example, immunoassays designed to aid in early diagnosis of a neoplastic or hyperplastic disorder, e.g. the presence of cancerous cells in the sample, e.g. PV-infected cells, e.g. PV-transformed cells, e.g. PV-immortalized cells, e.g. to detect cells in which a lesion of the E6-BP gene has occurred.

Another application of anti-E6-BP antibodies is in the immunological screening of cDNA libraries constructed in expression vectors such as λgt11, λgt18–23, λZAP, and λORF8. Messenger libraries of this type, having coding sequences inserted in the correct reading frame and orientation, can produce fusion proteins. For instance, λgt11 will produce fusion proteins whose amino termini consist of β-galactosidase amino acid sequences and whose carboxy termini consist of a foreign polypeptide. Antigenic epitopes of a subject E6-BP can then be detected with antibodies, as, for example, reacting nitrocellulose filters lifted from infected plates with anti-E6-BP antibodies. Phage, scored by this assay, can then be isolated from the infected plate. Thus, the presence of E6-BP homologs can be detected and cloned from other sources, and alternate isoforms (including splicing variants) can be detected and cloned from human sources.

Moreover, the nucleotide sequence determined from the cloning of the subject E6-binding proteins from a human cell line will further allow for the generation of probes designed for use in identifying E6-BP homologs in other human cell types, as well as E6-BP homologs from other animals. For instance, the present invention also provides a probe/primer comprising a substantially purified oligonucleotide, wherein the oligonucleotide comprises a region of nucleotide sequence which hybridizes under stringent conditions to at least 10 consecutive nucleotides of sense or anti-sense sequence of one of SEQ ID Nos: 1–7, or naturally occurring mutants thereof. In preferred embodiments, the probe/primer further comprises a label group attached thereto and able to be detected, e.g. the label group is selected from the group consisting of radioisotopes, fluorescent compounds, enzymes, and enzyme co-factors. Such probes can be used as a part of a diagnostic test kit for identifying transformed cells, such as for measuring a level of an E6-BP nucleic acid in a sample of cells from a patient; e.g. measuring an E6-BP mRNA level; e.g. determining whether a genomic E6-BP gene has been mutated or deleted.

In addition, nucleotide probes can be generated from the cloned sequence of the subject E6-binding proteins, which allow for histological screening of intact tissue and tissue samples for the presence of an E6-BP mRNA. Similar to the diagnostic uses of anti-E6-BP antibodies, the use of probes directed to E6-BP mRNAs, or to genomic E6-BP sequences, can be used for both predictive and therapeutic evaluation of allelic mutations which might be manifest in, for example, neoplastic or hyperplastic disorders (e.g. unwanted cell growth). Used in conjunction with anti-E6-BP antibody immunoassays, the nucleotide probes can help facilitate the determination of the molecular basis for a developmental disorder which may involve some abnormality associated with expression (or lack thereof) of an E6-binding protein. For instance, variation in E6-BP synthesis can be differentiated from a mutation in the E6-BP coding sequence. Likewise, targeted destruction of the E6-BP by the papillomavirus E6 protein, as is believed to occur with p53, can be distinguished from E6 sequestering of the E6 binding protein (i.e. which can result in modification of the E6-BP cellular function).

For example, the present method provides a method for determining if a subject is at risk for a disorder characterized by unwanted cell proliferation. In preferred embodiments, the subject method can be generally characterized as comprising detecting, in a tissue of the subject (e.g. a human patient), the presence or absence of a genetic lesion characterized by at least one of (i) a mutation of a gene encoding one of the subject E6-BPs or (ii) the mis-expression of an E6-BP gene. To illustrate, such genetic lesions can be detected by ascertaining the existence of at least one of (i) a deletion of one or more nucleotides from a subject E6-BP gene, (ii) an addition of one or more nucleotides to such an E6-BP gene, (iii) a substitution of one or more nucleotides of an E6-BP gene, (iv) a gross chromosomal rearrangement of one of the subject E6-BP genes, (v) a gross alteration in the level of a messenger RNA transcript of an E6-BP gene, (vi) the presence of a non-wild type splicing pattern of a messenger RNA transcript of an E6-BP gene, and (vii) a non-wild type level of an E6-binding protein. In one aspect of the invention there is provided a probe/primer comprising an oligonucleotide containing a region of nucleotide sequence which is capable of hybridizing to a sense or antisense sequence of one of SEQ ID Nos: 1–7, or naturally occurring mutants thereof, or 5' or 3' flanking sequences or intronic sequences naturally associated with the subject E6-BP genes. The probe is exposed to nucleic acid of a tissue sample; and the hybridization of the probe to the sample nucleic acid is detected. In certain embodiments, detection of the lesion comprises utilizing the probe/primer in a polymerase chain reaction (PCR) (see, e.g., U.S. Pat. Nos. 4,683,195 and 4,683,202) or, alternatively, in a ligation chain reaction (LCR) (see, e.g., Landegran et al. (1988) Science, 241:1077–1080; and NaKazawa et al. (1944) PNAS 91:360–364) the later of which can be particularly useful for detecting point mutations in the E6-BP gene. Alternatively, the level of E6-binding protein can detected in an immunoassay.

Also, the use of anti-sense techniques (e.g. microinjection of antisense molecules, or transfection with plasmids whose transcripts are anti-sense with regard to an E6-BP mRNA or gene sequence) can be used to investigate role of each of the subject E6-BP in HPV-mediated events (infection, transformation and/or immortalization), as well as the normal cellular function of each of the novel E6-BPs, e.g. in cell proliferation by inhibiting endogenous production of a particular E6-binding protein. Such techniques can be utilized in cell culture, but can also be used in the creation of transgenic animals.

Furthermore, by making available purified and recombinant E6-binding proteins, the present invention facilitates the development of assays which can be used to screen for drugs which are either agonists or antagonists of the normal cellular function of the subject E6-binding proteins, or of their role in papillomavirus infection. In one embodiment, the assay is derived to score for the ability of a compound to inhibit binding between a E6-BP and an E6 protein, e.g. E6 from a high risk HPV. A variey of assay formats will suffice and, in light of the present invention. will be readily apparent to the skilled artisan. For example, in one such screening assay the compound of interest is contacted with an isolated and purified E6-binding protein of the present invention. The mixture of the compound and E6-BP is then added to a composition containing the E6 protein but which does not contain E6-BP. Detection and quantification of labelled E6/E6-BP complexes provides a means for determining the compound's efficacy at inhibiting complex formation between the papillomavirus E6 protein and the subject E6-BP. Conveniently, a control assay is also performed to provide a baseline for comparison. In the control assay, isolated and purified E6-BP is added to a composition containing the E6, and the formation of E6/E6-BP complex is quantitated in the absence of the test compound.

Complex formation between the E6-BP and an E6 may be detected by a variety of other methods as well. For example, glutathione-S-transferase/E6 (GST/E6) fusion proteins are adsorbed onto glutathione sepharose beads which are then combined with an $^{35}$S-labeled E6-binding protein and incubated under conditions conducive to complex formation, e.g., at 4° C. in a buffer of 25 mM Tris-HCl (pH 7.2), 50 mM NaCl and 0.2% NP-40. Following incubation, the beads are washed to remove any unbound E6-BP, and the sepharose bead-bound radiolabel determined directly (e.g. beads placed in scintilant), or in the supernantant after the E6/E6-BP complexes are dissociated (e.g. by treatment with DTT). The supernatant containing the complexes can optionally be seperated by SDS-PAGE gel before detection.

Additionally, the subject E6-binding proteins can be used to generate an interaction trap assay, as described in the examples below (see also, U.S. Pat. No. 5,283,317; Zervos et al. (1993) Cell 72:223–232; Madura et al. (1993) J Biol Chem 268:12046–12054; Bartel et al. (1993) Biotechniques 14:920–924; and Iwabuchi et al. (1993) Oncogene 8:1693–1696), for subsequently detecting agents which disrupt binding of the E6-BP to an E6 protein. The interaction trap assay relies on reconstituting in vivo a fuctional transcriptional activator protein from two separate fusion proteins, one of which comprises the DNA-binding domain of a transcriptional activator fused to an E6 protein. The second protein comprises a transcriptional activation domain (e.g. able to initiate RNA polymerase transcription) fused to one of the subject E6-binding proteins. When the E6 and E6-binding protein interact, the two domains of the transcriptional activator protein are brought into sufficient proximity as to cause transcription of a reporter gene. In an illustrative embodiment, Saccharomyces cerevisiae YPB2 cells are transformed simultaneously with a plasmid encoding a GAL4db-E6 fusion and with a plasmid encoding the GAL4ad domain fused to a subject E6-BP. Moreover, the strain is transformed such that the GAL4-responsive promoter drives expression of a phenotypic marker. For example, the ability to grow in the absence of histidine can depends on the expression of the HIS3 gene. When the HIS3 gene is placed under the control of a GAL4-responsive promoter, relief of this auxotrophic phenotype indicates that a functional GAL4 activator has been reconstituted through the interaction of E6 and the E6-BP. Thus, agent able to inhibit E6-BP interaction with E6 will result in yeast cells unable to growth in the absence of histidine. Alternatively, the phenotypic marker (e.g. instead of the HIS3 gene) can be one which provides a negative selection when expressed such that agents which disrupt E6/E6-BP interactions confer positive growth selection to the cells.

Moreover, in instances wherein one of the subject E6-binding proteins possess an enzymatic activity, inhibitors of the enzymatic activity can be identified using assays derived from measuring the ability of an agent to inhibit catalytic converstion of a substrate by the subject enzyme.

In another aspect, the invention features transgenic non-human animals which express a recombinant E6-BP gene of the present invention, or which have had one or more of the subject E6-BP gene(s), e.g. heterozygous or homozygous, disrupted in at least one of the tissue or cell-types of the animal.

In another aspect, the invention features an animal model for developmental diseases, which has an E6-BP allele which is mis-expressed. For example, a mouse can be bred which has an E6-BP allele deleted, or in which all or part of one or more E6-BP exons are deleted. Such a mouse model can then be used to study disorders arising from mis-expressed E6-BP genes.

Exemplification

The invention now being generally described, it will be more readily understood by reference to the following examples which are included merely for purposes of illustration of certain aspects and embodiments of the present invention, and are not intended to limit the invention.

To identify genes encoding proteins that associate with HPV16 E6 protein, we employed a modified two-hybrid system that utilizes a genetic selection for genes encoding interacting proteins (see, for example, Fields et al. (1989) Nature 340:245–246; Chien et al. (1991) PNAS 88:9578–9582; Morrissey et al. (1989) J Virol 63:4422–5; and Lamberti et al. (1990) EMBO J 9:1907–1913). We have adapted this "two-hybrid system" by starting with a yeast strain expressing an HPV-16 E6/bovine papillomavirus (BPV) E2 DNA-binding domain (E2R) fusion protein ("E6-E2R") and a lacZ reporter driven by a promoter containing four E2 binding elements. The E6-E2R fusion protein can bind the E2 binding sites but does not induce expression of the reporter gene. This strain was then transformed with a library of plasmids in which randomly primed HeL a cell cDNA were inserted C-terminal to the strong VP16 transcription activation domain (Dalton et al. (1992) Cell 68:597–612). VP16/cDNA fusion proteins that can interact with E6-E2R, or that can bind the reporter promoter directly, would recruit the VP16 activation domain to the E2 binding sites and activate expression of the lacZ gene, and these yeast cells would subsequently stain blue on x-gal plates.

After screening approximately approx. $10^6$ independent yeast colonies, 40 were identified that became blue on galactose/x-gal. The VP16/cDNA plasmids were recovered after transformation into E. coli. These VP-16/cDNA genes were introduced into fresh yeast that contained the E2 reporter gene along with either the E6-E2 hybrid gene, a control vector, or the portion of the E2 gene used in the initial chimera. Results of this analysis indicated that some of the VP-16/cDNAs interact with the BPV E2 portion of the hybrid, others encoded proteins that activated the reporter gene even in the absence of E6-E2, while nine were found to reproducibly stimulate lacZ expression only in the presence of the HPV 16 E6-E2. Some of the 40 clones did not activate the reporter expression under any of these conditions, and in general, these were from the lightest blue colonies on the initial screen. We have also made a chimera with an N-terminus consisting of the 202 amino acid LexA DNA binding domain and in frame with HPV 16 E6. Using a yeast strain that has a chromosomal LexA dependent promoter which regulates the Leu2 gene, we have found that growth on leucine deficient media could be provided by all six VP-16 cDNAs, while several control VP-16 chimeras were non-viable. This provides additional evidence that the cDNAs interact with HPV 16 E6.

The cDNA plasmids that specifically interacted with E6 were subjected to DNA sequence analysis using a primer initiating within the VP16 coding sequence. This provides information on the reading frame at the fusion point with the cDNA. In general using this primer we have determined about 200–300 nucleotides of DNA sequence. In all cases an in frame open reading frame has been identified. We are also sequencing with the appropriate primers the 3' end of the cDNA insert. On three occasions the same gene was found twice. These differed at the point of the fusion with the VP16 activation domain and hence were not exact duplicates of the same library clone but instead represented independent isolates.

The SD-7 clone encoded an open reading frame of 210 amino acid residues with a HDEL signal sequence at the carboxy terminal. The 5' portion of SD7 was used as a probe to isolate the full-length cDNA from a HeLa lambda phage library. Several clones with overlapping inserts were isolated. These resulted in the recovery of cDNAs that together spanned 2 kb. Thus a complete copy of cDNA encoding the SD-7 protein was obtained. The nucleotide sequence and deduced amino acid sequence of the SD-7 cDNA clone is presented in the appended sequence listing. Besides the HDEL signal sequence in the carboxy terminal, there are 4 EF-hands in the C' half of E6-BP.

Northern blot analyses under high stringency conditions with SD7 sequence (or all cDNA fragments) hybridize to a transcript of 2,000 nucleotides in size that is present at similar levels in all the cell lines tested. Furthermore, SD-7 mRNA levels do not vary even in cell lines transformed by papillomavirus E6 genes.

To confirm further the in vivo association of E6 with the subject E6-binding proteins, in vitro binding assays were performed using in vitro translated E6 and immobilized GST-E6BP. For example, we observe that GST-SD7 and GST alone were used as positive and negative controls, respectively. GST-E6-BP binds HPV16 E6 to an extent comparable to that observed with E6-AP, while GST alone does not bind to HPV16 E6.

With the DNA sequence of the 5' and 3' end of the cDNA, we searched the GenBank/EMBL data bases for homology with previously cloned and sequenced genes. This computer search has revealed that some of the cDNAs are derived from known genes, while at least eight (clones SD 7, 8, 12, 16, 22, 28 and 32) are novel genes. Two have potential metal binding motifs which we speculate could be involved in loading zinc onto the E6 peptide. One has not been cloned from human but is related to a member of the proteolytic machinery and we suspect could complex with E6/E6-AP. Data from study of multiple HPV 16 E6 mutations cloned as E2 chimeras indicate that there is specificity in the interaction: some mutants remain positive with some VP16 cDNAs, while others are negative. This information further supports the validity of these clones.

Furthermore, a deposit of each of these clones as a library of pRS306 plasmids (designated "pRS306-E6BP") containing the 8 different novel clones isolated in the E6 interaction trap has been made with the American Type Culture Collection (Rockville, Md.) on Jul. 8, 1994, under the terms of the Budapest Treaty. ATCC Accession number 75827 has been assigned to the deposit. With this deposit in hand, one of ordinary skill in the art can generate the subject recombinant E6-BP genes and express recombinant forms of the subject E6-binding proteins. For instance, each of the E6-binding proteins of the present invention can be amplified from ATCC deposit no. 75827 by PCR using the following primers:

5'-TAC ATT AGG TCC TTT GTA GC-3' (SEQ ID No. 15)

5'-GGC GTG AAT GTA AGC GTG AC-3' (SEQ ID No. 16)

which prime amplification of the cDNA insert by hybridizing upstream of the VP-16 gene and downstream of the cDNA insert, respectively. The primer 5'G CAG ATG TTT ACC GAT GCC C-3' (SEQ ID No. 17)

which primes within the VP16 gene and near the VP16/cDNA boundary, can also be used to isolate the clones of the ATCC deposit.

Moreover, it will be immediately evident to those skilled in the art that, in light of the guide to the 5' (and in some instances the 3' ends) to each of the clones provided in Table 1, each individual clone of the ATCC deposit can be isolated using primers based on the nucleotide sequences provided by SEQ ID Nos. 1–7, or a combination of such primers and the primers of SEQ ID Nos. 15, 16 and 17.

Isolated clones can be subcloned into expression vectors in order to produce a recombinant protein, or can be used to generate anti-sense constructs, or can be used to generate oligonucleotide probes. In an illustrative embodiment, oligonucleotide probes have been generated using the coding sequences for each of the clones of the subject ATCC deposit, and used in Southern hybridization and in situ hybridization assays to detect the pattern and abundance of expression of each of the E6-binding proteins.

Moreover, because each member of the ATCC deposit is a plasmid encoding a fusion protein identified from an interaction trap assay, the clone can be utilized directly from the deposit in a similar ITS employed as, for examples a drug screening assay, or alternatively, a mutagenesis assay for mapping E6 binding epitopes.

TABLE 1

Guide to pRS306-E6BP

| Clone | Nucleotide Sequence | Peptide Sequence | Name |
|---|---|---|---|
| SD-7 | SEQ ID No. 1 | SEQ ID No. 8 | E6-BP$^{SD-7}$ |
| SD-8 | SEQ ID No. 2 | SEQ ID No. 9 | E6-BP$^{SD-8}$ |
| SD-12 | SEQ ID No. 3 | SEQ ID No. 10 | E6-BP$^{SD-12}$ |
| SD-16 | SEQ ID No. 4 | SEQ ID No. 11 | E6-BP$^{SD-16}$ |
| SD-22 | SBQ ID No. 5 | SEQ ID No. 12 | E6-BP$^{SD-22}$ |
| SD-28 | SEQ ID No. 6 | SEQ ID No. 13 | E6-BP$^{SD-28}$ |
| SD-32 | SEQ ID No. 7 | SEQ ID No. 14 | E6-BP$^{SD-32}$ |

Bacterial and Yeast Strains

*E. coli* DH5 α (supE44, ΔlacU169 (80lacZdeltaM15), hsdR17, recA1, endA1, gyrA96, thi1, relA1) were the transformation recipient for all plasmid constructions unless otherwise indicated. Yeast strain DBY1 was derived from BGW1-7a (MATα leu2-3 leu2-112 his4-519 ade1-100 ura3-52) by inactivating of the TRP1 gene. DBY1 was used as a host for the yeast two-hybrid system.

Plasmids

The URA selection gene in pBY-4 was inactivated by digestion with Stu I and replaced with the LEU2 gene from plasmid CV-13 (Morrissey et al. (1989) *J Virol* 63:4422–4425) to make pL-72. pE6E2T was constructed by inserting Bam HI-Sal I fragment containing the HPV-16E6 gene fused at its C-terminus to the BPV E2 DNA binding domain from pKPHPV16E6E2 into the Bam HI and Sal I sites of pYEplac112G pYEplac112GE2-R was made from pYEplac112GE2 by deletion of Nco I fragments that contains BPV-1 E2 activation domain.

pGEX plasmids (Pharmacia were used for expression of GST fusion proteins. For Example, pGSTSD7 was constructed by ligating polymerase chain reaction (PCR) products of the SD7 clone into pGEX-3T. pGST6E6 and pGST16E6 were constructed by ligation of the HPV6 E6 and HPV16 E6 open reading frames into pGEX-2T. Plasmid encoding GST-E6-AP have been previously described (Huibregtse et al (1993) *Mol Cell Biol* 13:4918–4927, 1993). pSP65 plasmid were used for cloning genes for in vitro transcription/translation. pSPBPVE6, pSP8E6 and pSP31E6 were constructed by ligation of the BPV-1 E6, HPV8 E6 and HPV31 E6 open reading frames into proper sites of pSP65. pSP6E6 and pSP16E6 have been described (Crook et al. (1991) *Cell* 67:547–556). pSP11E6 and pSP18E6 have also been described (Werness et al. (1990) *Science* 248:76–79). pSP7 contains E6-BP fragment from pSD7 in pSP65.

Library Screening

All yeast transformations were done by the lithium acetate method (Schiestl et al. (1989), *Curr Genet* 16:339–346). The yeast strain DBY1 was transformed with pL-72 and pE6E2T to generate strain DLE6E2, which was maintained under selection for the LEU2+ and TRP1+ markers. DLE6E2 cells were then transformed with a library of yeast shuttle vector plasmids in which randomly primed HeLa cell cDNA was inserted C-terminal to the VP16 transcription activation domain. Transformants were plated on trp−, ura−, and leu− selective minimal medium (YMM) containing 2% glucose as a carbon source. After 48–72 hr incubation at 30° C., colonies were transferred on filters to fresh plates containing selective medium and 2% galactose and incubated for an additional 18 hr to induce E6E2 and VP16/cDNA expression. The filters were then transferred to plates containing selective medium 2% galactose as well as X-gal. Color development time ranged from 8 to 24 hr, during which blue colonies were picked and processed as follows.

The VP16/cDNA plasmids were recovered from positive (blue) colonies after incubation in ura− selective liquid YMM containing 2% glucose for a week or more and subsequently transformed into DH5α. These VP16/cDNA genes were introduced into fresh DLE6E2 or yeast that contained the pL-72 along with pE2-R (DLE2-R). Those clones that result in a blue colony only in DLE6E2 but not DLE2-R were considered E6 specific and were studied further.

cDNA Cloning and Sequencing

To obtain cDNAs containing the full-length coding sequence of E6-binding proteins, a random-primed (Clontech) as well as a poly-d(T) primed keratinocytes cDNA libraries in λgt11 were screened at high stringency with $^{32}$P-labeled 5' fragments of the E6-BPs prepared using a random primers labeling kit with the non radioactive label, digoxigenin-dUTP (Boehringer Mannheim). Several positive lambda clones were isolated and inserts were subcloned into pBluescript II KS ± as a Sac I-Kpn I fragment or pUC19 as PCR products. Double-stranded DNA was sequenced by the dideoxy chain termination method (Sanger et al. (1977) *PNAS* 74:5463–5467) using Sequenase reagents (U.S. Biochemical). Comparison of the sequence with the data bases was performed using GCG (Genetics Computer Group) FASTA program.

Protein Expression and Antibodies

Glutathione S-transferase (GST) fusion proteins were expressed in *E. Coli* strain DH5α or JM109. One liter cultures were inoculated with 100 ml of stationary culture and grown for 1 hr before induced with 0.2 mM IPTG for 3 hr. Cells were harvested by centrifugation, resuspended in 50 ml of low salt association buffer (LSAB, 100 mM Tris-HCl, pH8.0, 100 mM NaCl, 1% NP-40, and 1 mM phenylmethylsulfonyl fluoride) plus 0.03% SDS, 2 mM DTT, and lysed by sonication. After centrifugation at 10,000 g for 10 min., supernatant were collected and mixed with glutathione Sepharose (Pharmacia). The mixture were rotated at 4° C. for 2 hr. The beads were then collected by centrifugation at 1000 g for 2 min., washed three times with 20 volume of LSAB, stored at 4° C.

In vitro-translated proteins were prepared by using the rabbit reticulocyte lysate translation system (Promega) and $^{35}$S-labeled cysteine or methionine (ICN).

A GST-SD7 fusion protein was purified and used to inject a rabbit. Serum were collected and used for immunoprecipitation.

In Vitro Binding

For in vitro binding, 30 μl of glutathione Sepharose containing approximately 2 μg of GST fusion proteins were combined with 2–20 μl of $^{35}$S-labeled in vitro translated proteins in LSAB in a total volume of 250 μl. The mixtures were rotated for 3 hr at 4° C. The mixtures were then washed six times with LSAB, boiled in SDS-gel loading buffer, and electrophoresed on SDS-polyacrylamide gels. Gels were fixed, soaked in autofluor (Dupont), dried, and exposed to Kodak XAR films. Gels were also scanned with a Molecular Dynamic Phosphor Imager.

All of the above-cited references and publications are hereby incorporated by reference.

SEQUENCE LISTING ( 1 ) GENERAL INFORMATION:

( i i i ) NUMBER OF SEQUENCES: 17

( 2 ) INFORMATION FOR SEQ ID NO:1:

( i ) SEQUENCE CHARACTERISTICS:
        ( A ) LENGTH: 1192 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:1:

```
GGATCCCACC   TGTAATCACC   AAGAAATTCT   TCCAAACTAA   CAAATCACGG   TCGACGGTGG        60

CGCGACGGCT   GGAGCGCGTG   AGTATCGGCG   GAATTCCGGA   CTTGGACTCA   GATGGCTTGG       120

TCACTGAAAG   GAACTCAGTT   CATGGATTCA   GATGTCTTTT   AAGCATTATG   CTATGCAAGA       180

AGCAAAACAA   CAGTTTGTTG   AATATGATAA   AAACAGTGAT   GATACTGTGA   CTTGGGATGA       240

ATATAACATT   CAGATGTATG   ATCGTGTGAT   TGACTTTGAT   GAGAACACTG   CTCTGGATGA       300
```

-continued

| | | | | | |
|---|---|---|---|---|---|
| TGCAGAAGAG | GAGTCCTTTA | GGAAGCTTCA | CTTAAAGGAC | AAGAAGCGAT | TTGAAAAAGC | 360 |
| TAACCAGGAT | TCAGGTCCCG | GTTTGAGTCT | TGAAGAATTT | ATTGCTTTTG | AGCATCCTGA | 420 |
| AGAAGTTGAT | TATATGACGG | AATTTGTCAT | TCAAGAAGCT | TTAGAAGAAC | ATGACAAAAA | 480 |
| TGGTGATGGA | TTTGTTAGTT | TGGAAGAATT | TCTTGGTGAT | TACAGGTGGG | ATCCAACTGC | 540 |
| AAATGAAGAT | CCAGAATGGA | TACTTGTTGA | GAAAGACAGA | TTCGTGAATG | ATTATGACAA | 600 |
| AGATAACGAT | GGCAGGCTTG | ATCCCCAAGA | GCTGTTACCT | TGGGTAGTAC | CTAATAATCA | 660 |
| GGGCATTGCA | CAAGAGGAGG | CGCTTCATCT | AATTGATGAA | ATGGATTTGA | ATGGTGACAA | 720 |
| AAAGCTCTCT | GAAGAAGAGA | TTCTGGAAAA | CCCGGACTTG | TTTCTCACCA | GTGAAGCCAC | 780 |
| AGATTATGGC | AGACAGCTCC | ATGATGACTA | TTTCTATCAT | GATGAGCTTT | AATCTCCGAG | 840 |
| CCTGTCTCAG | TAGAGTACTG | GCTCCTTTTA | TAATTTGTTA | CCAGCTTTAC | TTTTGTGATA | 900 |
| AAATATTGAT | GTTGTATTTT | ACACTCTTAA | GTCTTAACCA | CAGTCAGAAT | TATCTTAATG | 960 |
| TAGATTATAA | TTTTGGTCTT | TTAGGAAAAA | AAAACAAAAA | TCTGATATTT | ATTTCAAAAC | 1020 |
| GTATTGAAGC | AACAAAATAT | TAATATTGTG | CCATATGACA | ACAAAGTCTT | TCCTAAATAC | 1080 |
| TCCATCTGTT | TAGTACTGTA | TTGTGGAATA | TTTGAGTTCT | ATTTCCATAC | TTGAAAACAT | 1140 |
| GGAGGATTTT | AGAGATGCCT | GAACAATATT | ATTAAGTAG | TATGTGACCG | AG | 1192 |

( 2 ) INFORMATION FOR SEQ ID NO:2:

( i ) SEQUENCE CHARACTERISTICS:
( A ) LENGTH: 688 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:2:

| | | | | | |
|---|---|---|---|---|---|
| CCATCTCTAA | CGAAGTGCCG | GAGCCCCATG | TGTATCCCCT | GTCTCTAATC | ATGTTTATGA | 60 |
| GCGGCGGCTC | ATCGACAAGT | ACATTGCGGA | GAATGGTACC | GACCCCATCA | CAACCAGCC | 120 |
| TCTCTCCGAG | GAGCAGCTCA | TCGACATCTG | GCTGCCTCCA | TTTCCTTCTG | GACCACCAAT | 180 |
| AATGGCCCCA | CCACCTCCCA | TATGTCCAGA | TTCTGTTGAT | GATGCTGATG | CTTTGGGAAG | 240 |
| TATGTTAATT | TATGGTACAG | AGTGGCTATA | TACGGCTATA | TATGGTTGTC | GGAGGAGCAG | 300 |
| CTCATCGGAC | ATCAAAGTTG | CTCACCCAAT | CCGGCCCAAG | CCTCCCTCAG | GCCACCAGCA | 360 |
| TCCCGGCCAT | TCTGAAAGCT | TTGCAGGATG | AGTGGGATGC | AGTCATGCTG | CACAGCTTCA | 420 |
| CTCTGCGCCA | GCAGCTGCAG | ACAACCCGCC | AAGAGCTGTC | ACACGCTCTG | TACCAGCACG | 480 |
| ATGCCGCCTG | CCGTGTCATT | GCCCGTCTCA | CCAAGGAAGT | CACTGCTGCC | CGAGAAGCTC | 540 |
| TGGCTACCCT | GAAACCACAG | GCTGGCCTCA | TTGTGCCCCA | GCTGTGCCAA | GTTCCCAACC | 600 |
| AAGTGTTGTG | GGTGCGGGTG | AGCCAATGGA | TTTGGGTGAG | CTGGTGGGAA | TGACCCCAGA | 660 |
| GATTATTCAG | AAGCTTCAAG | ACAAAGCC | | | | 688 |

( 2 ) INFORMATION FOR SEQ ID NO:3:

( i ) SEQUENCE CHARACTERISTICS:
( A ) LENGTH: 234 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:3:

| | | | | | |
|---|---|---|---|---|---|
|CTTTTTTTT|TTTTTTGGC|TATTTTAATA|TTTTTTATTA|AGGGCTATAA|AAATACCCAG|60|
|AAGATAAATA|AATGTGATGC|AATGATATCT|GTCCTAATAT|GAAGAACTTT|CTTTCACTGC|120|
|ATTCTTTTCC|TTCACAATGG|CCTTCAAATC|ACAGGAGGCA|GTCATTCCAT|GCCATTTCCT|180|
|CTTCTTTTAT|TACACGCTAC|AGGATTTCCT|TTAGAGCACA|ATGGCTCGAG|ATCG|234|

( 2 ) INFORMATION FOR SEQ ID NO:4:

( i ) SEQUENCE CHARACTERISTICS:
        ( A ) LENGTH: 229 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:4:

| | | | | | |
|---|---|---|---|---|---|
|AAGGCGGCCG|ACAGGACAAG|GAGCATCCAA|GATACCTGAT|CCCAGAACTT|GCAAACAGTT|60|
|TTACCATTTA|GGCTGGGTCA|CTGGGACTGG|AGGAGGAATT|AGCTTGAAGC|ATGGGTGAAA|120|
|TCTACATTGC|TCCTTCAGGA|TGCAAAAGGA|ACGAATTCAG|CCTGAAGACA|TGTTTGTTTG|180|
|TGATATAAAT|GAAAAGGACA|TAAGTGGACC|TTCGCCATCG|AAGAAGCTA| |229|

( 2 ) INFORMATION FOR SEQ ID NO:5:

( i ) SEQUENCE CHARACTERISTICS:
        ( A ) LENGTH: 538 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:5:

| | | | | | |
|---|---|---|---|---|---|
|GCTACACTAG|AGCAGAGTAC|GAGTCTGAGG|CGGAGGGAGT|AATGGCAGGA|CAAGCGTTTA|60|
|GAAAGTTTCT|TCCACTCTTT|GACCGAGTAT|TGGTTGAAAG|GAGTGCTGCT|GAAACTGTAA|120|
|CCAAAGGAGG|CATTATGCTT|CCAGAAAAAT|CTCAAGGAAA|AGTATTGCAA|GCAACAGTAG|180|
|TCGCTGTTGG|ATCGGGTTCT|AAAGGAAAGG|GTGGAGAGAT|TCAACCAGTT|AGCGTGAAAG|240|
|TTGGAGATAA|AGTTCTTCTC|CCAGAATATG|GAGGCACCAA|AGTAGTTCTA|GATGACAAGG|300|
|ATTATTTCCT|ATTTAGAGAT|GGTGACATTC|TTGGAAAGTA|CGTAGACTGA|AATAAGTCAC|360|
|TATTGAAATG|GCATCAACAT|GATGCTGCCC|ATTCCACTGA|AGTTCTGAAA|TCTTTCGTCA|420|
|TGTAAATAAT|TTCCATATTT|CTCTTTTATA|ATAAACTAAT|GATAACTAAT|GACATCCAGT|480|
|GTCTCCAAAA|TTGTTTCCTT|GTACTGATAT|AAACACTTCC|AAATAAAAAT|ATGTAAAT|538|

( 2 ) INFORMATION FOR SEQ ID NO:6:

( i ) SEQUENCE CHARACTERISTICS:
        ( A ) LENGTH: 288 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:6:

| | | | | | |
|---|---|---|---|---|---|
|ATCAAAATAG|CCTGCTTGAC|GATGTTGTTT|AAATCAGACA|CCCACCCCTA|TTGTTATTCT|60|
|GAATGAGAGA|CACCTACCTG|TATTATCTTC|AGAGCAATGT|TCACAGATCG|GTCATGATTC|120|
|AAGTTTTTGT|TTGTTTCATT|GTCTCCTAAC|TGGTAAAATC|CATACACGCC|CATTTCAGTT|180|
|CATATTTATC|TTCATACCTG|TTGGGCCTAA|CATCGTTCCT|GATATATAGT|GGGTGTTCTA|240|

(2) INFORMATION FOR SEQ ID NO:7:

(i) SEQUENCE CHARACTERISTICS:
        (A) LENGTH: 255 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:7:

```
ACCCAAGTCA ATAGAAGCCG GCGTAAAGAG TGTTTTAGAT CACCCCTCC  CCAATAAAGC      60
TAAAACTCAC CTGAGTTGTA AAAAACTCCA GTTGACACAA AATAGACTAC GAAAGTGGCT     120
TTAACATATC TGAACACACA ATAGCTAAGA CCCAAACTGG ATTAGATACC CCACTATGCT     180
TAAGCCCTAA ACCTCAACAG TTAAATCAAC AAAACTGCTC GCCAGAACGC TGGGGCCACA     240
GCTTAAAACT CAAAG                                                     255
```

TAAATATTTA CTGAATGAAT AAGTTGGTTA ATGAGTAAAA TATAGGTT     288

(2) INFORMATION FOR SEQ ID NO:8:

(i) SEQUENCE CHARACTERISTICS:
        (A) LENGTH: 220 amino acids
        (B) TYPE: amino acid
        (D) TOPOLOGY: linear (ii) MOLECULE TYPE: peptide (v) FRAGMENT TYPE: N-terminal (xi) SEQUENCE DESCRIPTION: SEQ ID NO:8:

```
Met Gln Glu Ala Lys Gln Gln Phe Val Glu Tyr Asp Lys Asn Ser Asp
 1               5                  10                  15
Asp Thr Val Thr Trp Asp Glu Tyr Asn Ile Gln Met Tyr Asp Arg Val
            20                  25                  30
Ile Asp Phe Asp Glu Asn Thr Ala Leu Asp Ala Glu Glu Glu Ser
            35                  40                  45
Phe Arg Lys Leu His Leu Lys Asp Lys Lys Arg Phe Glu Lys Ala Asn
        50                  55                  60
Gln Asp Ser Gly Pro Gly Leu Ser Leu Glu Glu Phe Ile Ala Phe Glu
 65                  70                  75                  80
His Pro Glu Glu Val Asp Tyr Met Thr Glu Phe Val Ile Gln Glu Ala
                85                  90                  95
Leu Glu Glu His Asp Lys Asn Gly Asp Gly Phe Val Ser Leu Glu Glu
                    100                 105                 110
Phe Leu Gly Asp Tyr Arg Trp Asp Pro Thr Ala Asn Glu Asp Pro Glu
            115                 120                 125
Trp Ile Leu Val Glu Lys Asp Arg Phe Val Asn Asp Tyr Asp Lys Asp
        130                 135                 140
Asn Asp Gly Arg Leu Asp Pro Gln Glu Leu Leu Pro Trp Val Val Pro
145                 150                 155                 160
Asn Asn Gln Gly Ile Ala Gln Glu Glu Ala Leu His Leu Ile Asp Glu
                    165                 170                 175
Met Asp Leu Asn Gly Asp Lys Lys Leu Ser Glu Glu Glu Ile Leu Glu
                    180                 185                 190
Asn Pro Asp Leu Phe Leu Thr Ser Glu Ala Thr Asp Tyr Gly Arg Gln
            195                 200                 205
Leu His Asp Asp Tyr Phe Tyr His Asp Glu Leu Glx
```

|    | 210 | 215 | 220 |
|----|-----|-----|-----|

(2) INFORMATION FOR SEQ ID NO:9:

(i) SEQUENCE CHARACTERISTICS:
        (A) LENGTH: 216 amino acids
        (B) TYPE: amino acid
        (D) TOPOLOGY: linear (ii) MOLECULE TYPE: peptide (v) FRAGMENT TYPE: N-terminal (xi) SEQUENCE DESCRIPTION: SEQ ID NO:9:

```
Ile  Ser  Asn  Glu  Val  Pro  Glu  Pro  His  Val  Tyr  Pro  Leu  Ser  Leu  Ile
 1                  5                   10                  15

Met  Phe  Met  Ser  Gly  Gly  Ser  Ser  Ser  Thr  Leu  Arg  Arg  Met  Val
              20                  25                  30

Pro  Thr  Pro  Ser  Thr  Thr  Ser  Leu  Ser  Pro  Arg  Ser  Ser  Ser  Ser  Thr
              35                  40                  45

Ser  Gly  Cys  Leu  His  Phe  Leu  Leu  Asp  His  Gln  Xaa  Trp  Pro  His  His
     50                  55                  60

Leu  Pro  Tyr  Val  Gln  Ile  Leu  Leu  Met  Met  Leu  Met  Leu  Trp  Glu  Val
 65                 70                  75                  80

Cys  Xaa  Phe  Met  Val  Gln  Ser  Gly  Tyr  Ile  Arg  Leu  Tyr  Met  Val  Val
              85                  90                  95

Gly  Gly  Ala  Ala  His  Arg  Thr  Ser  Lys  Leu  Leu  Thr  Gln  Ser  Gly  Pro
              100                 105                 110

Ser  Leu  Pro  Gln  Ala  Thr  Ser  Ile  Pro  Ala  Ile  Leu  Lys  Ala  Leu  Gln
              115                 120                 125

Asp  Glu  Trp  Asp  Ala  Val  Met  Leu  His  Ser  Phe  Thr  Leu  Arg  Gln  Gln
     130                 135                 140

Leu  Gln  Thr  Thr  Arg  Gln  Glu  Leu  Ser  His  Ala  Leu  Tyr  Gln  His  Asp
145                      150                 155                 160

Ala  Ala  Cys  Arg  Val  Ile  Ala  Arg  Leu  Thr  Lys  Glu  Val  Thr  Ala  Ala
              165                 170                 175

Arg  Glu  Ala  Leu  Ala  Thr  Leu  Lys  Pro  Gln  Ala  Gly  Leu  Ile  Val  Pro
              180                 185                 190

Gln  Leu  Cys  Gln  Val  Pro  Asn  Gln  Val  Leu  Trp  Val  Arg  Val  Ser  Gln
              195                 200                 205

Trp  Ile  Trp  Val  Ser  Trp  Trp  Glu
     210                 215
```

(2) INFORMATION FOR SEQ ID NO:10:

(i) SEQUENCE CHARACTERISTICS:
        (A) LENGTH: 78 amino acids
        (B) TYPE: amino acid
        (D) TOPOLOGY: linear (ii) MOLECULE TYPE: peptide (v) FRAGMENT TYPE: N-terminal (xi) SEQUENCE DESCRIPTION: SEQ ID NO:10:

```
Leu  Phe  Phe  Phe  Phe  Leu  Ala  Ile  Leu  Ile  Phe  Phe  Ile  Lys  Gly  Tyr
 1                  5                   10                  15

Lys  Asn  Thr  Gln  Lys  Ile  Asn  Lys  Cys  Asp  Ala  Met  Ile  Ser  Val  Leu
              20                  25                  30

Ile  Xaa  Arg  Thr  Phe  Phe  His  Cys  Ile  Leu  Phe  Leu  His  Asn  Gly  Leu
          35                  40                  45
```

```
             Gln  Ile  Thr  Gly  Gly  Ser  His  Ser  Met  Pro  Phe  Pro  Leu  Leu  Leu  Leu
              50                      55                      60

His  Ala  Thr  Gly  Phe  Pro  Leu  Glu  His  Asn  Gly  Ser  Arg  Ser
              65                      70                      75
```

( 2 ) INFORMATION FOR SEQ ID NO:11:

( i ) SEQUENCE CHARACTERISTICS:
        ( A ) LENGTH: 75 amino acids
        ( B ) TYPE: amino acid
        ( D ) TOPOLOGY: linear ( i i ) MOLECULE TYPE: peptide ( v ) FRAGMENT TYPE: N-terminal ( x i ) SEQUENCE DESCRIPTION: SEQ ID NO:11:

```
             Gly  Gly  Arg  Gln  Asp  Lys  Glu  His  Pro  Arg  Tyr  Leu  Ile  Pro  Glu  Leu
              1                       5                       10                      15

Ala  Asn  Ser  Phe  Thr  Ile  Xaa  Ala  Gly  Ser  Leu  Gly  Leu  Glu  Glu  Glu
                                 20                      25                      30

Leu  Ala  Xaa  Ser  Met  Gly  Glu  Ile  Tyr  Ile  Ala  Pro  Ser  Gly  Cys  Lys
                            35                      40                      45

Arg  Asn  Glu  Phe  Ser  Leu  Lys  Thr  Cys  Leu  Phe  Val  Ile  Xaa  Met  Lys
              50                      55                      60

Arg  Thr  Xaa  Val  Asp  Leu  Arg  His  Arg  Ser
              65                      70                      75
```

( 2 ) INFORMATION FOR SEQ ID NO:12:

( i ) SEQUENCE CHARACTERISTICS:
        ( A ) LENGTH: 102 amino acids
        ( B ) TYPE: amino acid
        ( D ) TOPOLOGY: linear ( i i ) MOLECULE TYPE: peptide ( v ) FRAGMENT TYPE: N-terminal ( x i ) SEQUENCE DESCRIPTION: SEQ ID NO:12:

```
             Met  Ala  Gly  Gln  Ala  Phe  Arg  Lys  Phe  Leu  Pro  Leu  Phe  Asp  Arg  Val
              1                       5                       10                      15

Leu  Val  Glu  Arg  Ser  Ala  Ala  Glu  Thr  Val  Thr  Lys  Gly  Gly  Ile  Met
                                 20                      25                      30

Leu  Pro  Glu  Lys  Ser  Gln  Gly  Lys  Val  Leu  Gln  Ala  Thr  Val  Val  Ala
                            35                      40                      45

Val  Gly  Ser  Gly  Ser  Lys  Gly  Lys  Gly  Gly  Glu  Ile  Gln  Pro  Val  Ser
              50                      55                      60

Val  Lys  Val  Gly  Asp  Lys  Val  Leu  Leu  Pro  Glu  Tyr  Gly  Gly  Thr  Lys
              65                      70                      75                      80

Val  Val  Leu  Asp  Asp  Lys  Asp  Tyr  Phe  Leu  Phe  Arg  Asp  Gly  Asp  Ile
                                 85                      90                      95

Leu  Gly  Lys  Tyr  Val  Asp
                            100
```

( 2 ) INFORMATION FOR SEQ ID NO:13:

( i ) SEQUENCE CHARACTERISTICS:
        ( A ) LENGTH: 95 amino acids
        ( B ) TYPE: amino acid
        ( D ) TOPOLOGY: linear ( i i ) MOLECULE TYPE: peptide (v) FRAGMENT TYPE: N-terminal (xi) SEQUENCE DESCRIPTION: SEQ ID NO:13:

| Gln | Asn | Ser | Leu | Leu | Asp | Asp | Val | Val | Xaa | Ile | Arg | His | Pro | Pro | Leu |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Leu | Leu | Phe | Xaa | Met | Arg | Asp | Thr | Tyr | Leu | Tyr | Tyr | Leu | Gln | Ser | Asn |
|     |     |     | 20  |     |     |     | 25  |     |     |     |     | 30  |     |     |     |

| Val | His | Arg | Ser | Val | Met | Ile | Gln | Val | Phe | Val | Cys | Phe | Ile | Val | Ser |
|     |     | 35  |     |     |     |     | 40  |     |     |     |     | 45  |     |     |     |

| Xaa | Leu | Val | Lys | Ser | Ile | His | Ala | His | Phe | Ser | Ser | Tyr | Leu | Ser | Ser |
|     | 50  |     |     |     |     | 55  |     |     |     |     | 60  |     |     |     |     |

| Tyr | Leu | Leu | Gly | Leu | Thr | Ser | Phe | Leu | Ile | Tyr | Ser | Gly | Cys | Ser | Ile |
| 65  |     |     |     |     | 70  |     |     |     |     | 75  |     |     |     |     | 80  |

| Asn | Ile | Tyr | Xaa | Met | Asn | Lys | Leu | Val | Asn | Glu | Xaa | Asn | Ile | Gly |
|     |     |     |     | 85  |     |     |     |     | 90  |     |     |     |     | 95  |

(2) INFORMATION FOR SEQ ID NO:14:

(i) SEQUENCE CHARACTERISTICS:
      (A) LENGTH: 84 amino acids
      (B) TYPE: amino acid
      (D) TOPOLOGY: linear (ii) MOLECULE TYPE: peptide (v) FRAGMENT TYPE: N-terminal (xi) SEQUENCE DESCRIPTION: SEQ ID NO:14:

| Pro | Ser | Gln | Xaa | Lys | Pro | Ala | Xaa | Arg | Val | Phe | Xaa | Ile | Thr | Pro | Ser |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Pro | Ile | Lys | Leu | Lys | Leu | Thr | Xaa | Val | Lys | Asn | Ser | Ser | Xaa | His |
|     |     |     | 20  |     |     |     | 25  |     |     |     |     | 30  |     |     |

| Lys | Ile | Asp | Tyr | Glu | Ser | Gly | Phe | Asn | Ile | Ser | Glu | His | Thr | Ile | Ala |
|     |     | 35  |     |     |     |     | 40  |     |     |     |     | 45  |     |     |     |

| Lys | Thr | Gln | Thr | Gly | Leu | Asp | Thr | Pro | Leu | Cys | Leu | Ser | Pro | Lys | Pro |
|     | 50  |     |     |     |     | 55  |     |     |     |     | 60  |     |     |     |     |

| Gln | Gln | Leu | Asn | Gln | Gln | Asn | Cys | Ser | Pro | Glu | Arg | Trp | Gly | His | Ser |
| 65  |     |     |     |     | 70  |     |     |     |     | 75  |     |     |     |     | 80  |

| Leu | Lys | Leu | Lys |

(2) INFORMATION FOR SEQ ID NO:15:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: other nucleic acid (xi) SEQUENCE DESCRIPTION: SEQ ID NO:15:

TACATTAGGT CCTTTGTAGC                      20

(2) INFORMATION FOR SEQ ID NO:16:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: other nucleic acid -continued (xi) SEQUENCE DESCRIPTION: SEQ ID NO:16:

GGCGTGAATG TAAGCGTGAC 20

(2) INFORMATION FOR SEQ ID NO:17:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: other nucleic acid (xi) SEQUENCE DESCRIPTION: SEQ ID NO:17:

GCAGATGTTT ACCGATGCCC 20

Equivalents

Those skilled in the art will recognize, or be able to ascertain using no more than routine experimentation, many equivalents to the specific embodiments of the invention described herein. Such equivalents are intended to be encompassed by the following claims.

We claim:

1. An assay for screening test compounds to identify agents which modulate the binding of an E6-BP polypeptide with a papillomavirus E6 protein comprising:
   i. combining, as a cell-free system, an E6 protein or fragment thereof which binds to an E6-binding protein, an E6-binding protein or fragment thereof which binds to said E6 protein, and a test compound, said E6-binding protein selected from the group consisting of SD-7 (SEQ ID No: 8), SD-8 (SEQ ID No: 9), SD-12 (SEQ ID No: 10), SD-16 (SEQ ID No: 11), SD-22 (SEQ ID No: 12), SD-28 (SEQ ID No: 13), SD-32 (SEQ ID No: 14), keratin-17, apoferritin, nucleophosamin, C protein of the ribonucleoprotein particle C, ribonucleoprotein E, proteasome subunit HC8, and complement decay-accelerating factor; and
   ii. detecting the formation of a complex comprising said E6 protein and said E6-binding protein,
wherein a change in the formation of said complex in the presence of said test compound is indicative of an agent that modulates interaction between an E6 and an E6-binding protein.

2. A method of identifying an agent which disrupts the ability of an E6-binding protein to bind an E6 protein of a papillomavirus, comprising:
   i. providing a two-hybrid assay system including a candidate agent, a first fusion protein comprising a papillomavirus E6, and second fusion protein comprising an E6-BP polypeptide selected from the group consisting of SD-7 (SEQ ID No: 8), SD-8 (SEQ ID No: 9), SD-12 (SEQ ID No: 10), SD-16 (SEQ ID No: 11), SD-22 (SEQ ID No: 12), SD-28 (SEQ ID No: 13), SD-32 (SEQ ID No: 14), keratin-17, apoferritin, nucleophosamin, C protein of the ribonucleoprotein particle C, ribonucleoprotein E, proteasome subunit HC8, and complement decay-accelerating factor, under conditions wherein said two hybrid assay is sensitive to interactions between said E6 portion of said first fusion protein and said E6-BP portion of said second polypeptide;
   ii. measuring a level of interactions between said fusion proteins in the presence of said candidate agent; and
   iii. comparing the level of interaction of said fusion proteins in the presence of said candidate agent to a level of interaction of said fusion proteins in the absence of the candidate agent,
wherein a decrease in the level of interaction in the presence of said candidate agent is indicative of an agent that inhibits interaction of a viral E6 protein with an E6-binding protein.

3. The assay of claim 1, wherein said cell-free system is a cell lysate.

4. The assay of claim 1, wherein said cell-free system is a reconstituted protein mixture.

5. The method of claim 1, wherein said E6 protein is a human papillomavirus (HPV) E6 protein.

6. The method of claim 5, wherein said HPV is a high risk HPV.

7. The method of claim 6, wherein said HPV is selected from a group consisting of HPV-16 or HPV-18.

8. The method of claim 1, wherein one or both of said E6 and E6-binding protein is a fusion protein.

9. The method of claim 8, wherein said fusion protein is a Glutathione-S-transferase fusion protein.

10. The method of claim 1, wherein at least one of said E6 and E6-binding protein comprises an endogenous detectable label for detecting the formation of said complex.

11. The method of claim 2, wherein said E6 protein is a human papillomavirus (HPV) E6 protein.

12. The method of claim 11, wherein said HPV is a high risk HPV.

13. The method of claim 12, wherein said HPV is selected from a group consisting of HPV-16 or HPV-18.

14. The method of claim 2, wherein said two hybrid assay system comprises a reporter construct includes a transcriptional control element responsive to one of an E2 protein, a Gal4 protein, or a LexA protein, and one of said first or second fusion protein includes a portion which binds said transcriptional control element.

15. An assay for screening test compounds to identify agents which modulate the binding of an E6-binding protein with a papillomavirus E6 protein comprising:
   i. providing a cell expressing a papillomavirus E6 protein or fragment thereof which binds to an E6-binding protein and a recombinant E6-binding protein or fragment thereof which binds to said E6 protein, said E6-binding protein selected from the group consisting of SD-7 (SEQ ID No: 8), SD-8 (SEQ ID No: 9), SD-12 (SEQ ID No: 10), SD-16 (SEQ ID No: 11), SD-22 (SEQ ID No: 12), SD-28 (SEQ ID No: 13), SD-32 (SEQ ID No: 14), keratin-17, apoferritin, nucleophosamin, C protein of the ribonucleoprotein particle C, ribonucleoprotein E, proteasome subunit HC8, and complement decay-accelerating factor;

ii. contacting the cell with a test compound; and iii. detecting the formation of a complex comprising said E6 protein and said E6-binding protein, wherein a change in the quantity of formation of said complex in the presence of said test compound is indicative of an agent that modulates the interaction between an E6 and an E6-binding protein.

16. An assay for screening candidate agent for potential inhibitors of the binding of an E6-BP polypeptide with a papillomavirus E6 protein, comprising:

i. generating a test system comprising (a) a first target polypeptide including an E6-BP portion having an amino acid sequence represented in SEQ ID No. 8, and (b) a second target polypeptide comprising an E6 polypeptide capable of binding to said E6-BP portion said first target polypeptide, under conditions wherein said first and second target polypeptides interact;

ii. contacting said test system with a candidate agent; and iii. detecting formation of a complex comprising said first and second target polypeptides, wherein inhibiting said complex formation is indicative of said candidate agent having a potential activity to inhibit interaction between the E6 and the E6-binding protein.

17. The method of claim 16, wherein one or both of said E6 and E6-binding protein is a fusion protein.

18. The method of claim 17, wherein said fusion protein is a Glutathione-S-transferase fusion protein.

19. The method of claim 16, wherein at least one of said E6 and E6-binding protein comprises an endogenous detectable label for detecting the formation of said complex.

20. The method of claim 16, wherein said E6 protein is a human papillomavirus (HPV) E6 protein.

21. The method of claim 20, wherein said HPV is a high risk HPV.

22. The method of claim 21, wherein said HPV is selected from a group consisting of HPV-16 or HPV-18.

23. The method of claim 15, wherein one or both of said E6 and E6-binding protein is a fusion protein.

24. The method of claim 23, wherein said fusion protein is a Glutathione-S-transferase fusion protein.

25. The method of claim 15, wherein at least one of said E6 and E6-binding protein comprises an endogenous detectable label for detecting the formation of said complex.

26. The method of claim 15, wherein said E6 protein is a human papillomavirus (HPV) E6 protein.

27. The method of claim 26, wherein said HPV is a high risk HPV.

28. The method of claim 27, wherein said HPV is selected from a group consisting of HPV-16 or HPV-18.

29. The method of claim 1, wherein said E6-binding protein is a fusion protein.

30. The method of claim 1, wherein said E6-binding protein is selected from the group consisting of SD-7, keratin-17, apoferritin, ribonucleoprotein E, proteasome subunit HC8, and complement decay-accelerating factor.

31. The method of claim 1, wherein said E6-binding protein is SD-7.

* * * * *